(12) United States Patent
Warenius et al.

(10) Patent No.: US 7,989,176 B2
(45) Date of Patent: Aug. 2, 2011

(54) TREATING CANCER

(75) Inventors: Hilmar Meek Warenius, Heswell (GB); Philip Spencer Rudland, Liverpool (GB); Laurence Anthony Seabra, Heswell (GB)

(73) Assignee: Theryte Ltd., Liverpool (GB)

( * ) Notice: Subject to any disclaimer, the term of this patent is extended or adjusted under 35 U.S.C. 154(b) by 153 days.

(21) Appl. No.: 10/508,873

(22) PCT Filed: Mar. 25, 2003

(86) PCT No.: PCT/GB03/01275
§ 371 (c)(1),
(2), (4) Date: Dec. 6, 2004

(87) PCT Pub. No.: WO03/081239
PCT Pub. Date: Oct. 2, 2003

(65) Prior Publication Data
US 2006/0003329 A1    Jan. 5, 2006

(30) Foreign Application Priority Data

Mar. 25, 2002  (GB) .................................. 0207031.6
Jul. 17, 2002   (GB) .................................. 0216634.6
Oct. 8, 2002    (GB) .................................. 0223325.2

(51) Int. Cl.
*G01N 33/574*    (2006.01)
(52) U.S. Cl. ...................................... 435/7.23; 435/6.14
(58) Field of Classification Search .................. None
See application file for complete search history.

(56) References Cited

U.S. PATENT DOCUMENTS 5,962,316 A * 10/1999 Beach et al. .................. 435/325
6,004,939 A * 12/1999 Chen et al. ....................... 514/43

FOREIGN PATENT DOCUMENTS

| WO | WO 98/49146 | * 11/1998 |
| WO | WO 99/27087 | * 6/1999 |
| WO | WO 99/42821 | * 8/1999 |

OTHER PUBLICATIONS

Haas et al, Oncogene, 1997, 15:179-192.*
Ceha et al, Biochem Biophys Res Comm, 1998, 249:550-555.*
NCBI protein sequence -cyclin-dependent kinase inhibitor 2A.*

* cited by examiner

*Primary Examiner* — Misook Yu
*Assistant Examiner* — Mark Halvorson
(74) *Attorney, Agent, or Firm* — Gavrilovich Dodd & Lindsey LLP; Joseph R. Baker, Jr.

(57) ABSTRACT

Provided is a method for screening for effective agents for the treatment of cancer which method comprises selecting a putative agent that is likely to disrupt a function mediated by a critical normal gene product, which function is required for the successful division and continued cell survival of cancer cells, and which function is not required for the successful division and continued cell survival of control cells, treating a cancer cell sample and a control cell sample with a purative agent and determining the cytotoxic effect of, and/or the growth inhibitory effect of the putative agent on these samples, and identifying an effective agent as an agent which is more cytotoxic to, and/or more inhibiting to the growth of the cancer cell sample than the control cell sample. This invention further provides an effective agent identified by this screening method and a method of treating a cancer patient with such an agent.

4 Claims, 13 Drawing Sheets

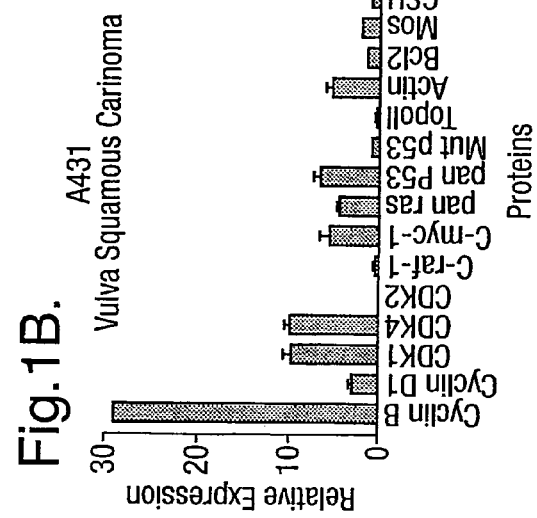
Fig. 1A. 2780 Ovarian Carcinoma
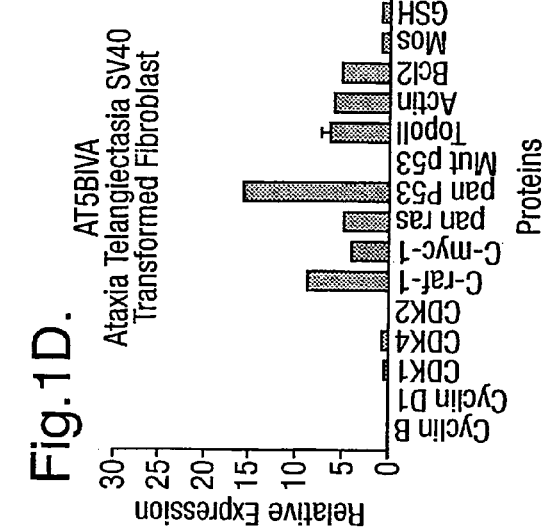
Fig. 1B. A431 Vulva Squamous Carinoma
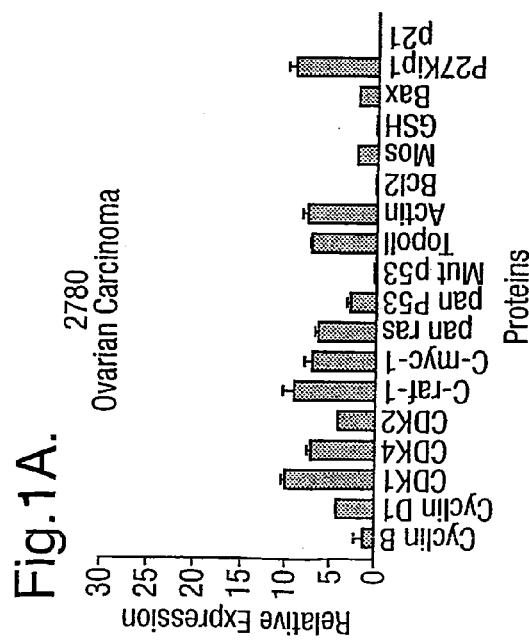
Fig. 1C. A549 Lung Adenocarcinoma
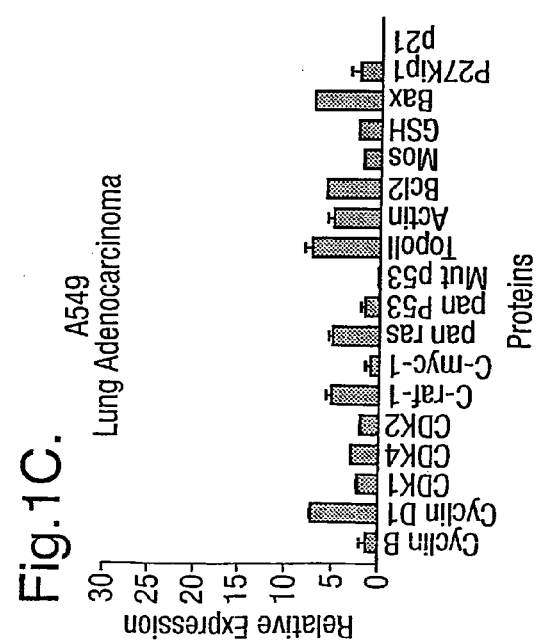
Fig. 1D. AT5BIVA Ataxia Telangiectasia SV40 Transformed Fibroblast

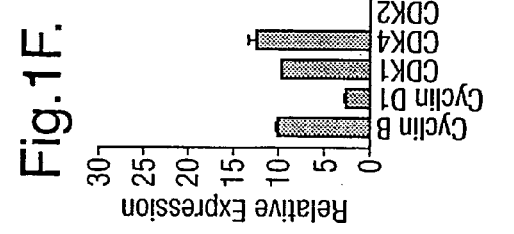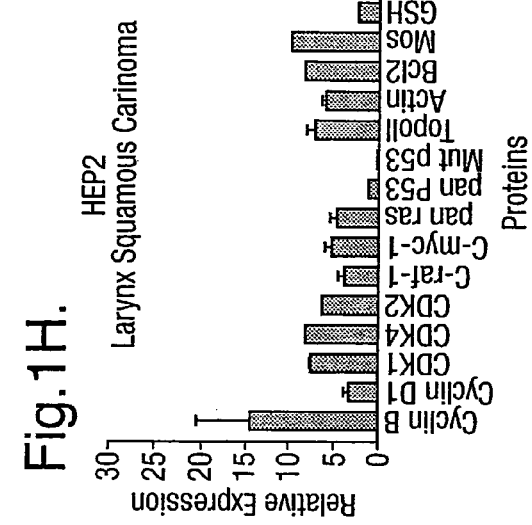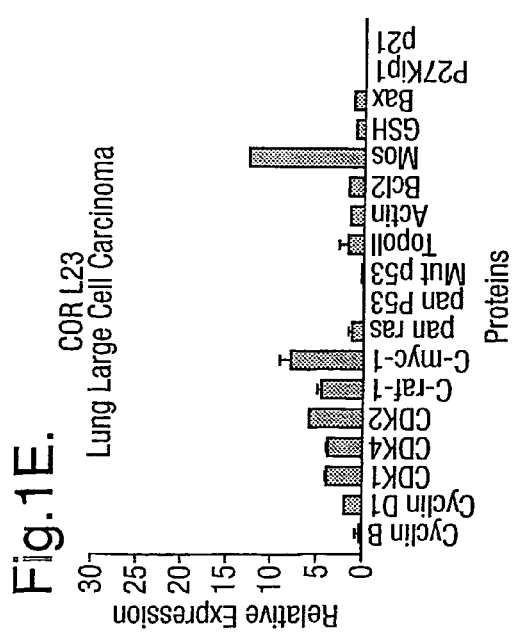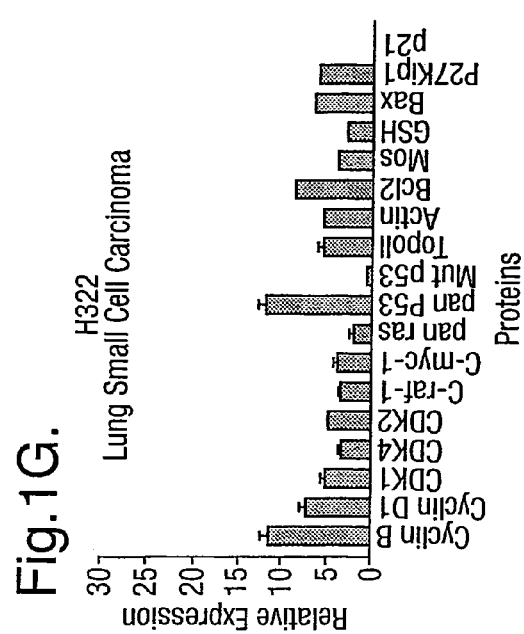

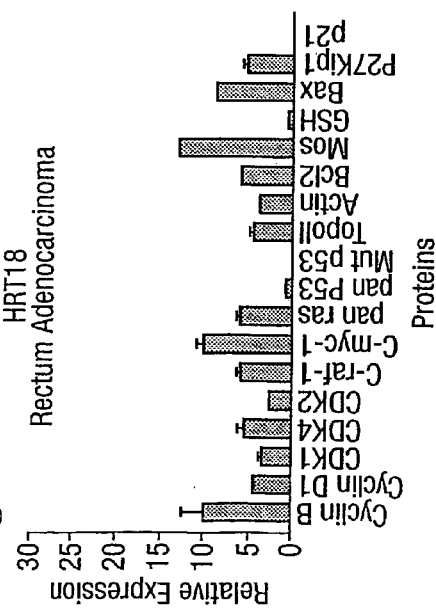
Fig. 1I.
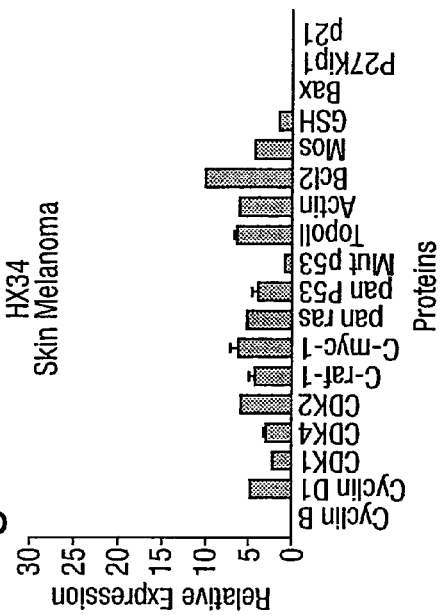
Fig. 1J.
Fig. 1K.
Fig. 1L.

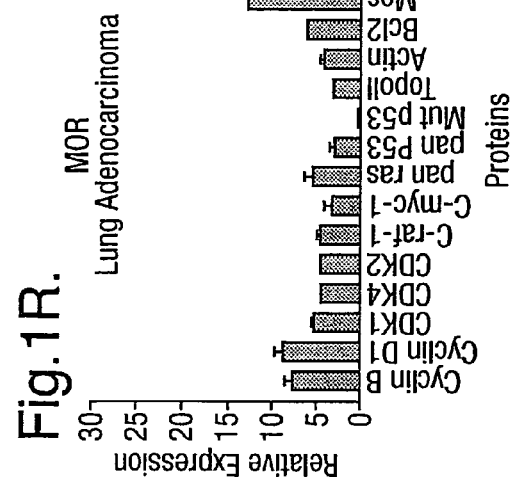
Fig. 1R. MOR Lung Adenocarcinoma
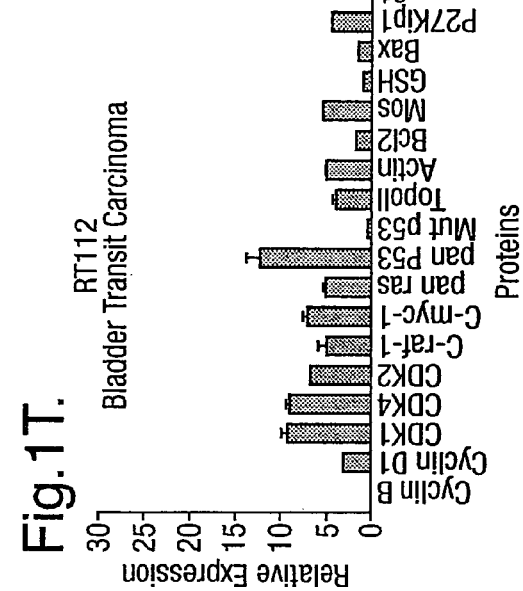
Fig. 1T. RT112 Bladder Transit Carcinoma
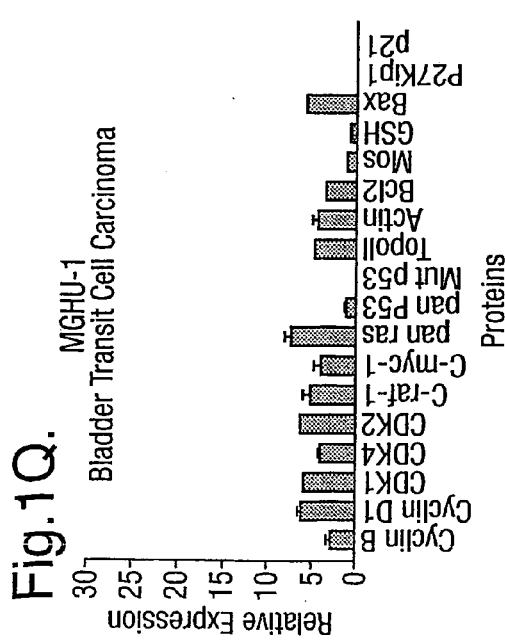
Fig. 1Q. MGHU-1 Bladder Transit Cell Carcinoma
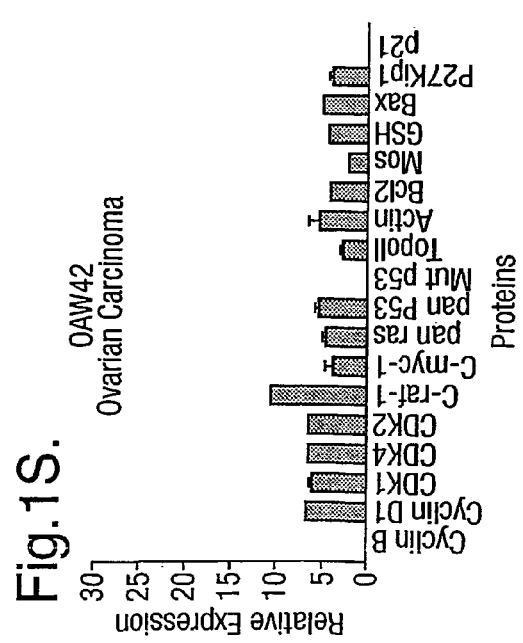
Fig. 1S. OAW42 Ovarian Carcinoma

Fig.4.

CDK4 PROTEIN STRUCTURE (303aa)

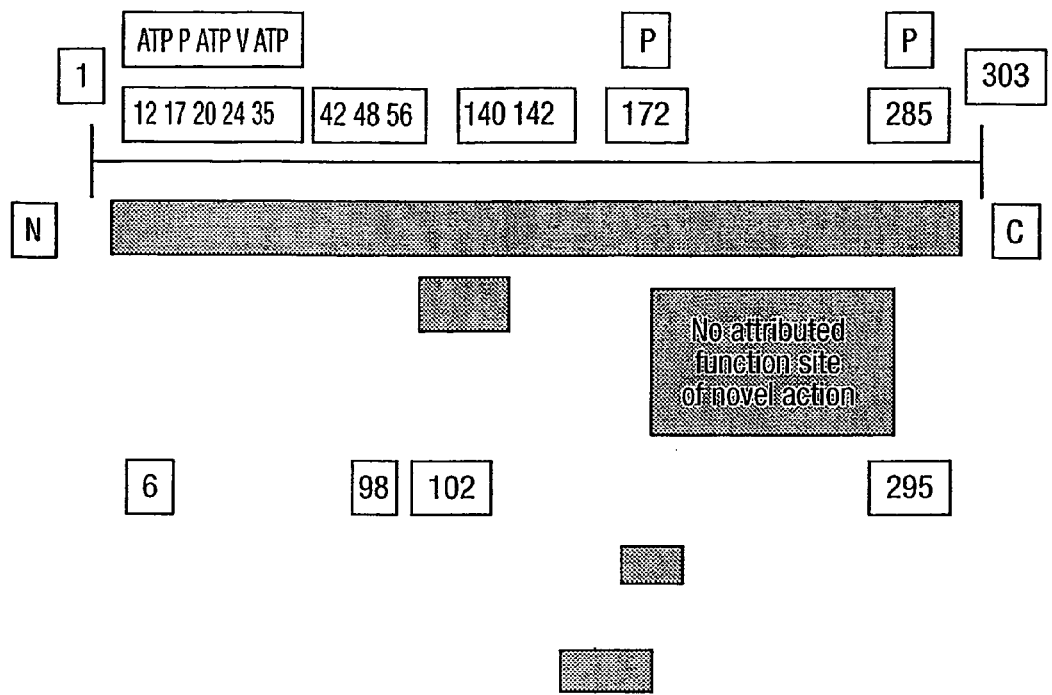

| | |
|---|---|
| 6-295 | Protein kinase domain |

12,20 & 35-ATP binding site

24(V)-p16$^{INK4A}$ Variant site (R->C in somatic and familial melanoma, generates Arg$^{24}$->cys, a dominant oncogene resistant to inhibition by p16)

42,48-polygly domain 56,140,142-active site

Gln98, Asp 99 Thr102-p16 binding region

17-Tyr phosphate binding site

172-Thr phosphate binding site (necessary for kinase activity)

285-Ser phosphate binding site

Fig.6.
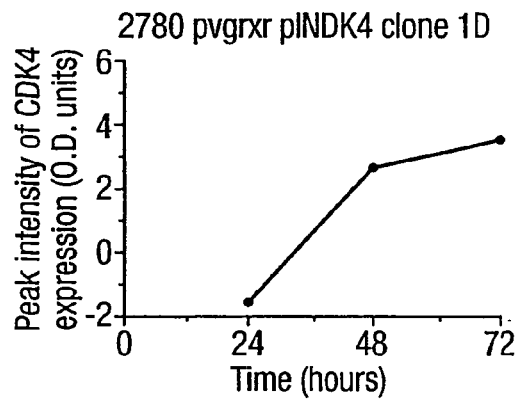
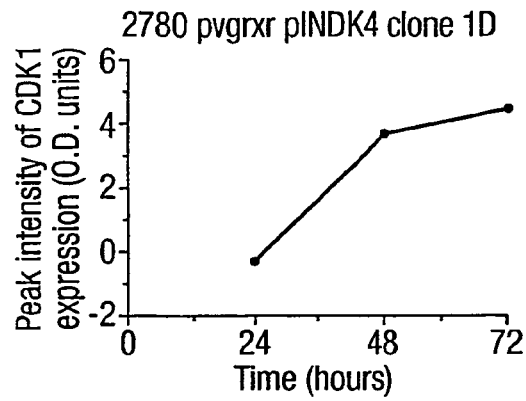
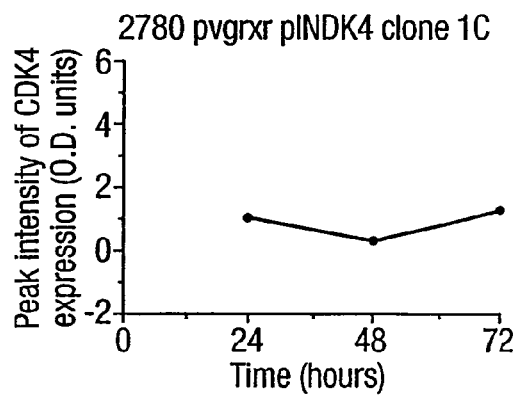
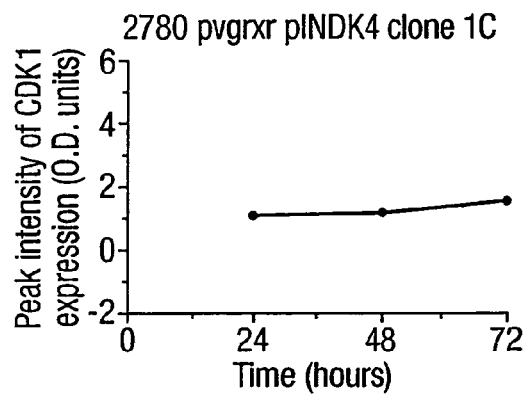
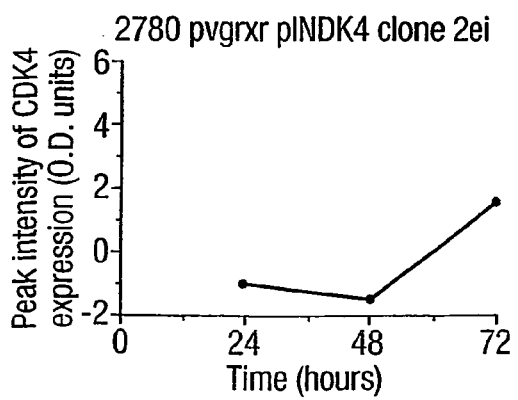
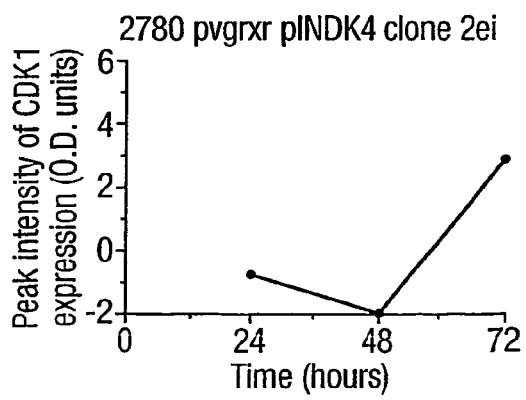

Fig. 8.

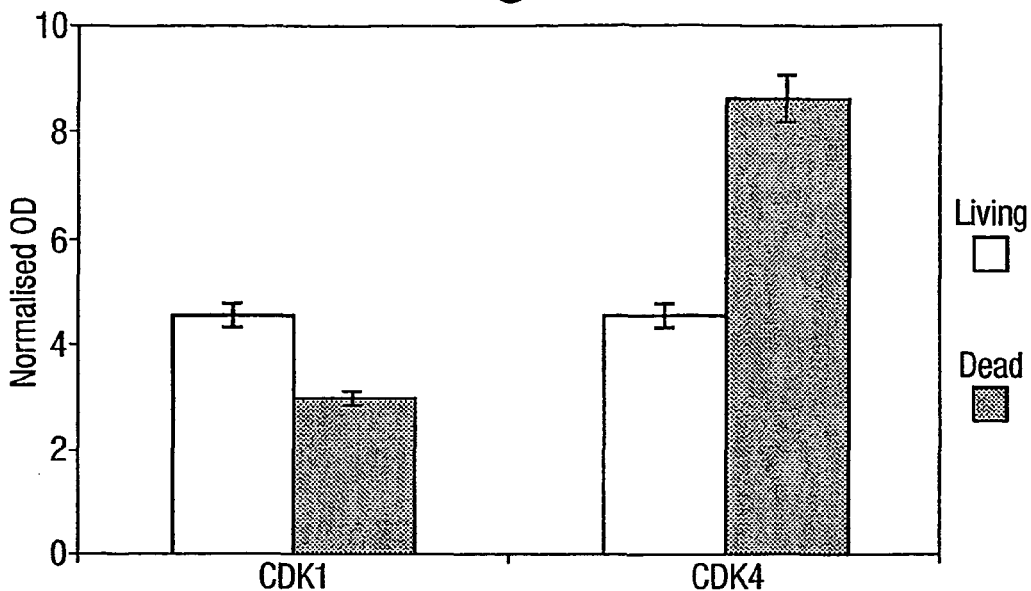

Fig. 11A.

Changes in protein expression of Phosphorylated Retinoblastoma Protein p110 [A] and p105 [B] following cell plating

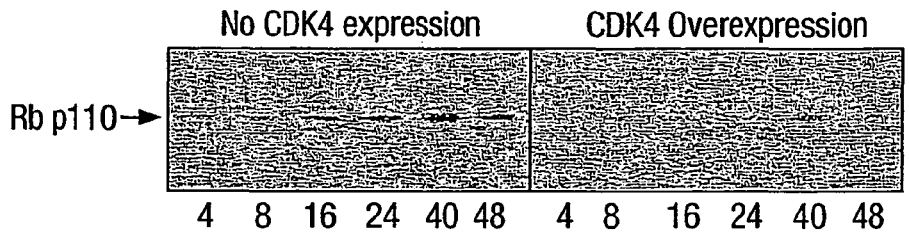

Fig. 11B.

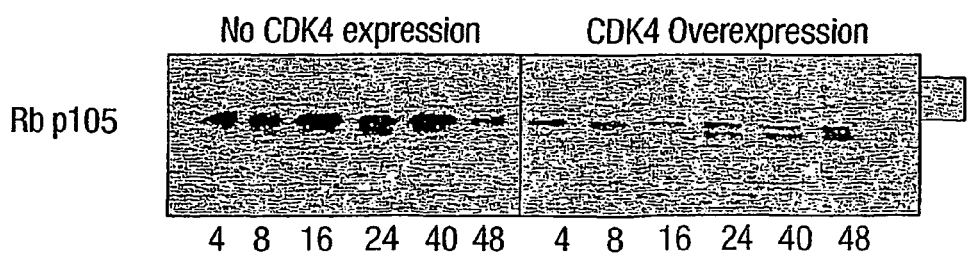

Changes in the Phosphorylated Retinoblastoma protein product p110 at times of 4, 8, 16, 24, 40 and 48 hours following cell plating. (pRb retinoblastoma p110 mouse monoclonal antibody IF8. Santa Cruz Biotechnology.CA.USA. pRb retinoblastoma p105 mouse monoclonal antibody NCL-RB-358. Novacastra. Tyneside. UK)

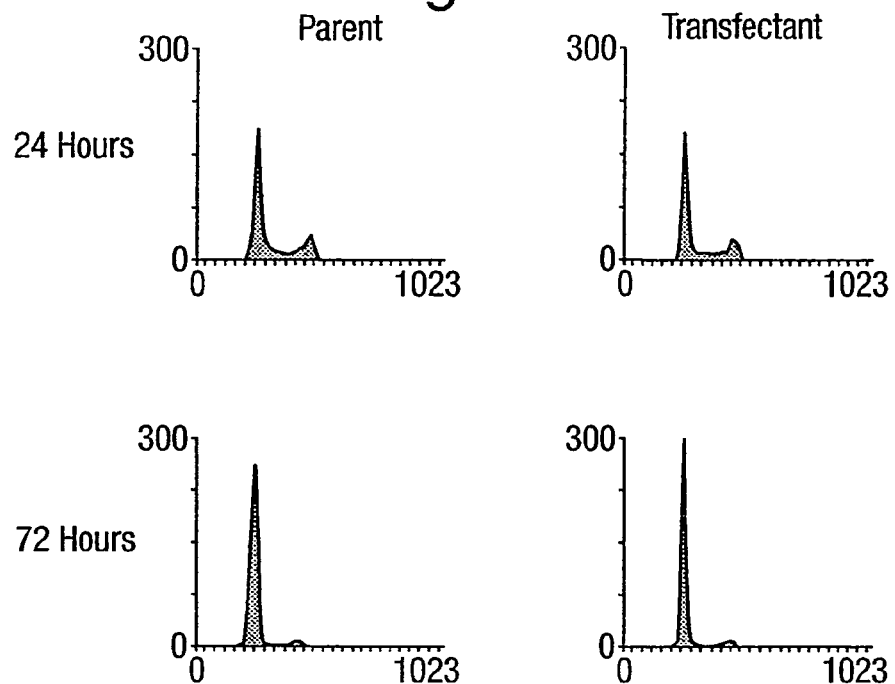
Fig. 9.
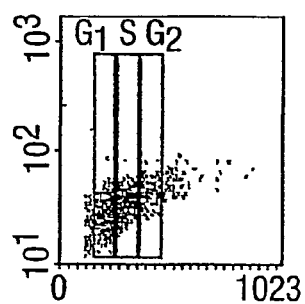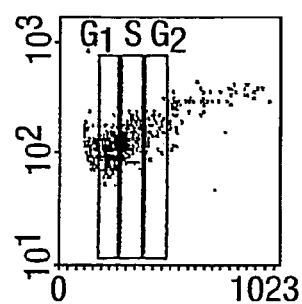
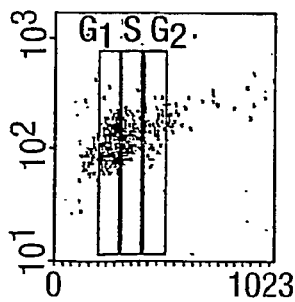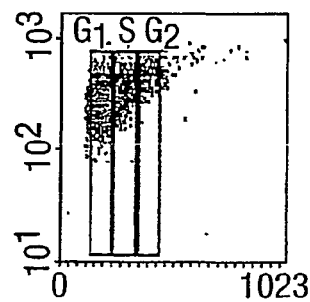

SEQUENCE LISTING

<160> NUMBER OF SEQ ID NOS: 4

<210> SEQ ID NO 1
<211> LENGTH: 18
<212> TYPE: DNA
<213> ORGANISM: Artificial

```
<220> FEATURE:
<223> OTHER INFORMATION: Phosphorothionate oligonucleotide
<220> FEATURE:
<221> NAME/KEY: misc_feature
<222> LOCATION: (1)..(18)
<223> OTHER INFORMATION: Sense phosphorothionate oligonucleotide having
      a sequence identical to a portion of the Rb mRNA

<400> SEQUENCE: 1
gtcatgccgc ccaaaacc                                                       18

<210> SEQ ID NO 2
<211> LENGTH: 18
<212> TYPE: DNA
<213> ORGANISM: Artificial
<220> FEATURE:
<223> OTHER INFORMATION: Phosphorothionate oligonucleotide
<220> FEATURE:
<221> NAME/KEY: misc_feature
<222> LOCATION: (1)..(18)
<223> OTHER INFORMATION: Antisense phosphorothionate oligonucleotide
      that is complementary to a portion of Rb mRNA

<400> SEQUENCE: 2
ggttttgggc ggcatgac                                                       18

<210> SEQ ID NO 3
<211> LENGTH: 32
<212> TYPE: DNA
<213> ORGANISM: Artificial
<220> FEATURE:
<223> OTHER INFORMATION: Oligonucleotide primers
<220> FEATURE:
<221> NAME/KEY: primer_bind
<222> LOCATION: (1)..(32)

<400> SEQUENCE: 3
cccgaattca gaatggtcac ctctcgatat ga                                       32

<210> SEQ ID NO 4
<211> LENGTH: 31
<212> TYPE: DNA
<213> ORGANISM: Artificial
<220> FEATURE:
<223> OTHER INFORMATION: Oligonucleotide primer
<220> FEATURE:
<221> NAME/KEY: primer_bind
<222> LOCATION: (1)..(31)

<400> SEQUENCE: 4
cccgcggccg ctgctcactc tggattacct t                                        31
```

TREATING CANCER

FIELD OF THE INVENTION

The present application concerns a method of selecting an effective agent for the treatment of cancer, including metastatic cancer. The application is particularly concerned with the identification of suitable targets for anti-cancer agents. More particularly, the application identifies a region of the CDK4 gene product responsible for a critical normal function of the gene product which is a suitable target for anti-cancer agents.

BACKGROUND TO THE INVENTION

Although chemotherapy has been responsible for curing many people of cancer in the latter half of the 20th century, there still remain a large number of patients whose tumours either show little response to treatment, or respond initially only to recur later. For these patients, the current treatments are clearly inadequate.

The majority of the deaths arising from cancers of solid tissues can be ascribed to the process of metastasis wherein cancer cells spread from the site of origin to distant sites in the body. For example, in breast cancer, cancer cells break off from the primary tumour and metastasise via lymphatic and blood vessels. The initial spread of cancer cells is usually to the local lymph nodes, most frequently to the adjacent axilla. Thereafter breast cancer cells can disseminate via the blood stream resulting in distant metastases. These distant metastases are usually the cause of death in the majority of breast cancer patients. Therefore, anti-cancer agents that prevent metastasis would be highly desirable.

There has been substantial investment in researching the mechanisms used by normal eukaryotic cells to control progress through the cell cycle in the hope that this would lead to an understanding of how cancer arises and suggest possible targets for cancer therapy. It is currently understood that progress through the phases of the cell cycle is controlled by a class of enzymes termed "Cyclin Dependent Kinases" (CDKs). Cyclin dependent kinases are serine/threonine cyclin-dependent kinases that are synthesised continuously and maintain relatively constant levels in the cell. They are inactive on their own. CDKs are activated upon binding to their cyclin partner (De Bondt et al. (1993) Nature, 363: 595-602; Jeffrey et al. (1995) Nature, 376: 313-320), and upon phosphorylation by a CAK (cyclin activating kinase; Grana and Reddy (1995) Oncogene, 11: 211-219). CDK kinase activity can be inhibited by removal of the kinase's cyclin partner and by an inhibitory phosphorylation of a tyrosine residue close to the N-terminus of the protein. For example, CDK4 protein is activated by phosphorylation of threonine 164 but inhibited by phosphorylation of tyrosine 17. The activity of a CDK/cyclin holoenzyme can be regulated by cyclin dependent kinase inhibitors (E1-Deiry et al. (1993) Cell, 75: 817-825; Harper et al (1993) Cell, 75: 805-816; Xiong et al. (1993) Nature, 366: 701-704; Polyak et al. (1994), Genes Dev. 8: 9-22; Serrano et al. (1993) Nature 366: 704-707; Serrano et al. (1995) Science, 267: 249-252).

The cell cycle has several checkpoints to ensure that a cell does not replicate its DNA or divide under inappropriate conditions (Hartwell and Weinert (1989) Science, 296: 629-634). Before passing through these checkpoints, a cell must meet certain criteria. Molecular pathways signaling the presence or absence of these criteria influence the decision to cross the checkpoint by affecting activation of the CDK/cyclin holoenzyme responsible for regulating passage through the checkpoint. For example, positive signal transduction pathways relaying signals from cell surface receptors, such as the Ras/Raf/Erk pathway have been demonstrated to influence pRb phosphorylation, through an effect on the cyclin/CDK holoenzymes regulating the G1/S checkpoint (Lloyd et al., (1997) Genes Dev. 11: 663-677). Conversely cyclin dependent kinase inhibitors (CDKIs) such as the $p16^{INK4}$, $p27^{KIP1}$ and $p21^{CIP1/WAF1}$ ene products can arrest cells at the G1/S checkpoint by inhibiting G1 cyclin/CDK holoenzymes. The $p21^{WAF1/CIP1}$ gene may be transcriptionally activated by p53 protein providing a mechanism by which p53 protein can arrest normal cells at the G1/S checkpoint (Li et al., (1994) Oncogene, 9: 2261-2268).

Once activated, the CDK/cyclin holoenzyme initiates the events needed for the cell to enter the next phase of the cell cycle. Different CDK/cyclin holoenzymes regulate different checkpoints in the cell cycle (Hunter and Pines (1994) Cell, 79: 573-582; Sherr (1994) Cell 79: 551-555). The initiation of progress from G1 to S phase that occurs when quiescent mammalian cells are stimulated to divide by the presence of growth factors, involves the interaction of the cyclin D family with either the CDK4 gene product or the CDK6 gene product depending on the cell type (Matushime et al. (1994) Mol. Cell Biol. 14: 2066-2076; Mayerson and Harlow (1994) Mol. Cell Biol. 14: 2077-2086). In mammals, other checkpoints are controlled by different CDK/cyclin holoenzymes e.g. late G1/S is regulated by CDK2/cyclin E, progress through S phase by CDK2/cyclin A and late S/G2 by CDK1/cyclin A (Jeffrey et al. (1995) Nature 376: 313-320). Transit from G2 to mitosis is controlled by the CDK1/cyclin B complex in both mammals and yeast (Draetta (1990) Trends Biochem. Sci. 15: 378-382; Murray (1992) Nature, 359: 599-604).

Activation of CDK4 is understood to initiate transit from G1 to S phase. FIG. 2 provides a schematic diagram showing the role of CDK4 at the G1/S transition in normal cells. Activated CDK4 is thought to mediate its effects through phosphorylation of pRb and related proteins p107 and p130. In their hypophosphorylated state pRb, p107 and p130 bind E2F transcription factors. However, upon phosphorylation of pRb, p107 and p130, E2F transcription factors are released (Hijmans et al. (1995). Mol. Cell Biol. 15: 3082-3089). The free E2Fs form heterodimers with the proteins DP-1/DP-2. The E2F/DP heterodimers then bind to DNA and activate transcription of factors required for DNA synthesis (Wu et al. (1995) Mol. Cell Biol. 2536-2546). In addition, free E2F protein upregulates genes controlling cell division such as cyclin E, cyclin A, CDK1 and E2Fs. Overexpression of some members of the E2F family, such as E2F-1, however, does not only promote increased cell division, but can also lead to apoptosis. Adenoviral-mediated transfer of exogenous DNA vectors overexpressing E2F-1 to human colonic adenocarcinoma (Draus et al., (2001), Exp. Mol. Med. 33: 209-219), oesophageal (Yang et al., (2000) Clin. Cancer Res. 6: 1579-1589), melanoma (Dong et al., (1999) Cancer 86: 2021-2033, glioma (Fueyo et al., (1998) Nat. Med. 4: 685-690), breast, ovarian (Hunt et al., (1997) Cancer Res., 57: 4722-4726 and head and neck (Liu et al., (1999) Cancer Gene Ther. 6: 163-171) cancer cell lines induced apoptosis in these cell lines. E2F-1 overexpression caused cells to enter S-phase prematurely and to accumulate in G2/M from which they subsequently exited by undergoing apoptosis.

During carcinogenesis, it is currently thought that normal cells become immortalised as a consequence of disruption of the positive and negative cell signalling pathways and cell cycle control mechanisms described above, for example, amplification and overexpression of cyclins and CDKs. Amplification and overexpression of cyclin D protein occurs in many human tumours (Lammie et al., (1991) Oncogene 6: 439-444, Jiang et al, (1993) Proc. Natl. Acad. Sci USA 90: 9026-9030, Schurring et al, (1992) Oncogene, 7: 355-361, Bartkova et al., (1995) Oncogene, 10: 775-778) and cell lines (Buckley et al., (1993) Oncogene, 8: 2127-2133, Warenius et al., (1996) Int. J. Cancer 67: 224-231. Unscheduled expression of cyclin BI and cyclin E in inappropriate phases of the cell cycle has also been reported in several leukaemic and solid tumour cell lines (Gong et al, (1994) Cancer Res. 54: 4285-4288). 20-fold amplification of genomic CDK4 DNA with accompanying increases in mRNA expression has been detected in 13.8% of a series of 29 human gliomas (He et al., (1994) Cancer Res. 53: 5535-5541). Similar increases in CDK4 genomic DNA and mRNA have been found in 2 out of 14 human sarcomas (Khatib et al., (1993) Cancer Res. 53: 5535-5541).

Abnormalities in CDK inihibitors particularly mutations and altered expression of $p16^{INK4}$ may also occur (Nobori et al., 1994, Okamoto et al., 1994 Jen et al., 1994). High levels of $p16^{INK4}$ protein have been found to correlate with functional inactivation of the retinoblastoma gene product (Tam et al., (1994) Cancer Res. 54: 5816-5820) whilst overexpression of the CDK4 gene product has been suggested to provide an alternative mechanism to $p16^{INK4}$ gene homozygous deletion.

In summary, it is believed that cancers may arise through an evolutionary process, selecting cells with gene mutations that provide a growth advantage (Ilyas et al. Eur. J. Cancer (1999) 35:335-351). By this means the normal diploid cell is progressively transformed into a fully-fledged cancer cell. Studies of early events in carcinogenesis have revealed several genetic lesions causing errors in the cell division and death pathways (Hanahan and Weinberg, Cell (2000) 100:57-70). Approximately three to seven separate molecular lesions are believed to be required to transform a normal diploid cell into a cancer cell (The Genetic Basis of Human Cancer (1999) Vogelstein and Kinzler, eds.).

A more advanced model of carcinogenesis has been proposed by Dr. Bernard Weinstein. Dr. Weinstein postulates that only certain patterns of gene expression enable cells to survive and replicate. Furthermore, it is postulated that the disruption of gene products that normally control cell division and death in early carcinogenesis results in the cell circuitry becoming "unbalanced". In order for the cancer cell to survive and divide, certain other genes may need to become upregulated. This model may explain why gene products that normally act to inhibit cell division (such as $p27^{KIP1}$ and pRb) are upregulated in certain cancer cells.

Cancer cells may metastasise from the site of origin to distant sites in the body. The protein (Kuukasjarvi et al. Cancer Res. (1997) 57:1597-1604) and mRNA populations (Hashimoto et al. Cancer Res. (1996) 56: 5266-5271) of metastatic and non-metastatic breast cancer cells have been compared in order to identify metastagenes; genes that are differently expressed in metastatic, relative to non-metastatic cells. Metastagenes code for proteins that contribute only to the potentially fatal metastatic spread of cancer cells. They do not contribute to uncontrolled growth or immortalisation. Metastagene products include enzymes such as proteases (Duff Clin. Exp. Metastasis (1992) 10:145-155), proteins associated with cell adhesion (Iwamura et al. Cancer Res. (1997) 57: 1206-1212) and motility factors (Cajot et al. Cancer Res. (1997) 57: 2593-2597; Meyer-Siegler and Hudson Urology (1996) 48: 448-452). An example of a protein thought to be associated with adhesion is osteopontin (Oates et al. Oncogene (1996) 13: 97-104, Oates et al. Cancer Metastasis Rev. (1997) 17: 1-15; Chen et al, Oncogene (1997) 14: 1581-1588) and one associated with motility is a regulatory calcium ion binding protein, p9ka (S100A4) (Barraclough et al. Eur. J. Biochem (1982) 129: 335-341; Barraclough et al. Nucleic Acids Res. (1984) 21:8097-8114; Ebralidze et al. Genes Dev. (1989) 3: 1086-1093; Gibbs et al. J. Biol. Chem. (1994) 269: 18992-18999).

Based on the present models of cancer and metastasis, attempts have been made at rational drug development. It has been considered that the gene products that are disrupted during carcinogenesis are likely to provide highly specific targets for cancer chemotherapy. Using the targets identified by this approach, new therapeutic agents are now being introduced into the clinic. These include Herceptin, which targets the her/neu cell surface receptor in breast cancer (Sliwkowski et al. (1999) Semin Oncol. 4 suppl.12: 60-70; Baselga Eur J. Cancer (2001) 37 suppl. 1:18-24), farnesyl transferase inhibitors which target the ras oncogene (Adjei et al. (2000) Cancer Research 60:1871-1877), ONYX015 (an E1B deletion mutant adenovirus), designed to target cancer cells with non-functional TP53 (Nemunaitis et al. (2000) Cancer Research 60:6359-6366), ST1571, designed to target the translocated abelson kinase in chronic myeloid leukaemia (Mauro and Druker (2001) Oncologist 6:233-238), and flavopiridol which inhibits the kinase activity of the CDK4 gene product.

Thus, the majority of targets for rational anti-cancer drug development available at present have been defined by studies of early carcinogenesis. However, in contrast to cells studied in early carcinogenesis, profound chromosomal damage can be found in the cell exhibiting the "full malignant phenotype". The full malignant phenotype is found in clinically advanced tumours. It is characterised by an enormous diversity of structural chromosome damage (The Genetic Basis of Human Cancer (1998) Vogelstein and Kinzler eds.; Mitelman et al (1997) Nature Genet 15:417-474). In addition, cells having the full malignant phenotype also have widespread changes in gene expression when compared to normal cells (Hough et al. (2000), Cancer Research 60: 6281-6287; Waghray et al (2001) Cancer Res. 61: 4283-4286; Wang et al. (2000) Oncogene 19:1519-1528). Given the number of genetic lesions producing molecular abnormalities within the a cancer cell having the full malignant phenotype, it seems unlikely that the cell can simply be returned to its pre-cancerous, normal diploid phenotype by selectively targeting and inhibiting these abnormal early cancer genes.

There are numerous problems associated with the current approach to rational anti-cancer drug development. These include multiplicity of potential drug targets, tumour heterogeneity and genetic instability.

The number of potential drug targets available to the current approach to rational anti-cancer drug development is large and growing. At present there is no way of telling which of the many abnormal genes and gene products present in a cell having the full malignant phenotype are ultimately likely to prove the most effective drug targets.

The difficulties with rational drug development against selected molecular targets are compounded by tumour heterogeneity. Tumour heterogeneity may result from the random chaotic nature of cell division in clinical tumours. It describes the situation where tumour cells of apparently the same type in different patients, behave differently and show differences in phenotypic expression of gene products including those implicated in the process of carcinogenesis (Shackney and Shankey (1995) Cytometry 21:2-5; Harada et al. (1998) Cancer Research 58-4694-4700). As a result of these differences in the phenotypic expression of gene products, apparently similar tumour cells in different patients may respond differently to a particular anticancer drug with some cells being sensitive whilst others are resistant. This type of drug resistance is called intrinsic resistance.

Even within the same tumour in an individual patient, all cells may not exhibit the same pattern of gene expression so that some cells may be resistant to a certain type of chemotherapy to which others are sensitive. Thus chemotherapy may initially cause tumour shrinkage by killing the sensitive cells but fail to kill the resistant cells. The remaining resistant cells continue dividing to produce a cancer that is now wholly drug resistant. This process is termed acquired resistance.

Therefore, tumour heterogeneity leads to intrinsic resistance and acquired resistance of cancers to new anticancer drugs. This may account for the relatively poor clinical response rates in phase I/II studies of new anticancer agents targeting molecules disrupted in early carcinogenesis. In fact, in one completed phase II study of flavopiridol in patients with advanced gastric cancer, no clinical responses were observed (Kaubisch et al. (2000) The Cancer Journal 6: 192-210)

Genetic instability is found in the majority of cancers, if not all. It results in new mutations occurring throughout the life of a tumour (Genetic Instability in Cancer (1996) Lindahl ed.; Lengauer et al. (1998) Nature 396: 643-649). Certain of these mutations may confer drug resistance to the cells in which they occur. Genetic instability, with its ongoing molecular changes is a further cause of acquired drug resistance and makes human tumours a moving target for the rational design of chemotherapeutic agents.

Therefore, currently available treatments are not always adequate to deal with all cancers. Furthermore, agents directed to gene products involved in early carcinogenesis are unlikely to prevent metastasis.

SUMMARY OF THE INVENTION

The present invention aims to overcome the problems associated with the above prior art, and in particular aims to solve the problems of tumour heterogeneity and genetic instability that limit the efficacy of prior art cancer therapies. Accordingly, the present invention provides a method of screening for an agent effective in the treatment of a cancer, which method comprises:
 a) selecting a putative agent that is likely to disrupt a function mediated by a critical normal gene product, which function is required for the successful division and continued cell survival of cancer cells, and which function is not required for the successful division and continued cell survival of control cells;
 b) treating a cancer cell sample and a control cell sample with the putative agent, and determining the cytotoxic effect of, and/or the growth inhibiting effect of the putative agent on these samples; and
 c) identifying an effective agent as an agent which is more cytotoxic to, and/or more inhibiting to the growth of the cancer cell sample than the control cell sample.

BRIEF DESCRIPTION OF THE FIGURES

The invention will now be described in more detail, by way of example only, with reference to the following figures.

FIG. 4 is a schematic diagram of the CDK4 gene product showing the ATP binding sites, the active site and the sites of phosphorylation. A region between 172 and 285 has no attributed function. This may be the region mediating the novel function of CDK4.

FIG. 6 shows the relationship between the expression level of the CDK4 and CDK1 gene products in a human ovarian cancer cell line. Ovarian cancer cell line 2780 was transfected with pVgRxR and full length wild type CDK4 DNA in pIND. Three transfected clones are depicted: Clone 1D/735 is a high CDK4 expressing transfectant in which marked induction of the CDK4 gene product can be achieved following ponasterone stimulation; clone 2ei is a low-expressing transfectant; and clone IC shows intermediate expression of the CDK4 gene product on ponasterone induction. Expression of the CDK4 gene product was induced by ponasterone treatment and the levels of the CDK1 and CDK4 gene products at various times after induction were measured by western blotting. It can be seen that the levels of the CDK1 and CDK4 gene products are approximately equal at all times in all clones. In particular, it can be seen that the levels of endogenous cellular CDK1 protein in clone 1D/735 are elevated following ponasterone induction of the expression of exogenous, transfected, CDK4 protein.

FIG. 8 shows the relationship between the levels of the CDK1 gene product and the CDK4 gene product in proliferating and dying L23COR cells. It can be seen that the ratio of the CDK1/CDK4 gene products in proliferating cells is approximately 1.0, while the ratio of CDK1/CDK4 in dying cells is approximately 0.3.

FIG. 9 shows propidium iodide histograms of uninduced and ponasterone-induced exponentially growing, asynchronously cultures of clone 2870 1D/35 at 24 h and 72 h after ponasterone induction/mock induction. It can be seen that CDK4 transfection does not alter the distribution of cells throughout the cell cycle phases G1, S and G2/M. In addition, there is no evidence of a subdiploid apoptotic cell population.

FIG. 10 shows bivariate analysis of CDK4 or CDK1 expression throughout the cell cycle in exponentially growing, asynchronous cultures of uninduced and ponasterone-induced clone 2780 1D/735. Both CDK4 and CDK1 proteins are expressed throughout the cell cycle (i.e. CDK4 expression is not limited to the G1 phase and CDK1 expression is not limited to G2 and M phase). It can be seen that in the cultures induced by ponasterone, the levels of both the CDK1 and CDK4 gene products are higher than in the corresponding uninduced cultures. Both the uninduced and induced cultures had a similar distribution of cells in each phase of the cell cycle.

FIG. 11 shows western blots of samples of uninduced and ponasterone-induced clone 2780 1D/735 at 4, 8, 16, 24, 40 and 48 h after induction/mock induction. Panel A is probed with an antibody specific for hyperphosphorylated pRb (p1110). Panel B is probed with an antibody raised against hypophosphorylated pRb (p105) that recognises both hyperphosphorylated and hypophosphorylated pRb. Panel A shows that in the uninduced clone 2780 1D/735, there is a low level of hyperphosphorylated pRb (p 110). In the induced clone, hyperphosphorylated pRb (p110) is virtually undetectable. Panel B shows that in the uninduced cell line (clone 2780 1D/735 not stimulated with ponasterone), most pRb is hyperphosphorylated. At 24 h after induction, however, the induced cell line contains both hyperphosphorylated and hypophosphorylated pRb.

DETAILED DESCRIPTION OF THE INVENTION

Figure 1M:
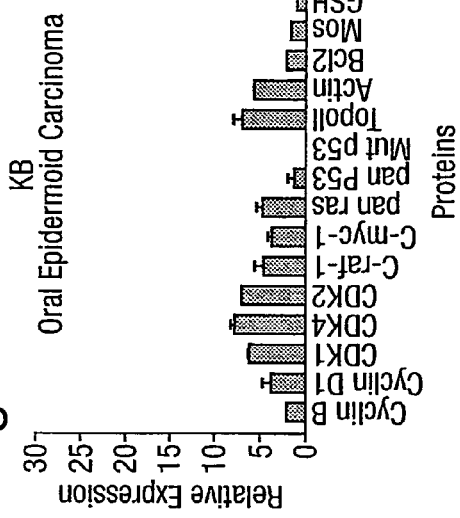
FIG. 1 shows histograms that display the level of expression of numerous gene products that control cell division and death in twenty individual human cancer cell lines. It can be seen that each cancer cell line has a different pattern of gene expression.
Figure 1N:
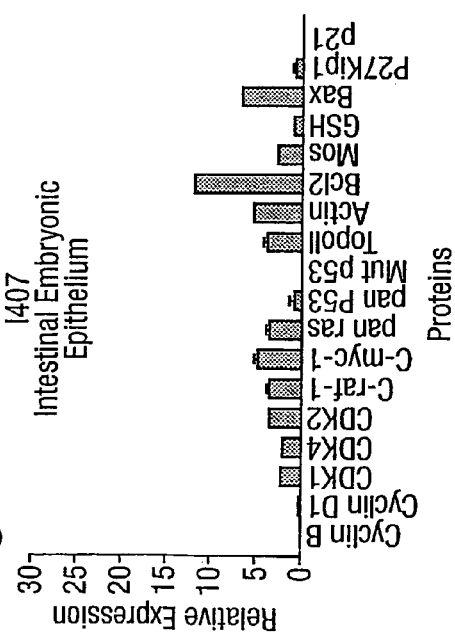
Figure 1O:
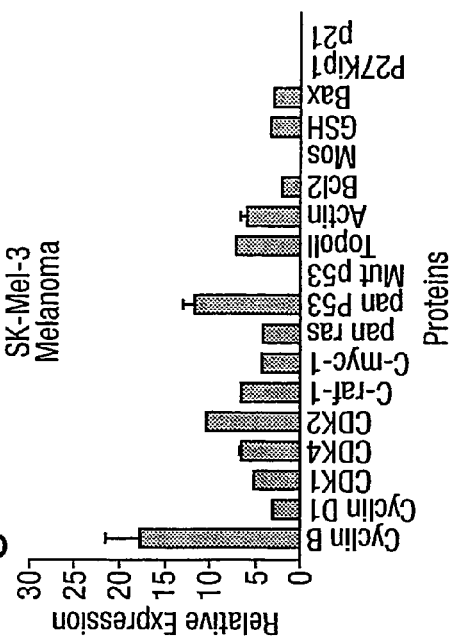
Figure 1P:
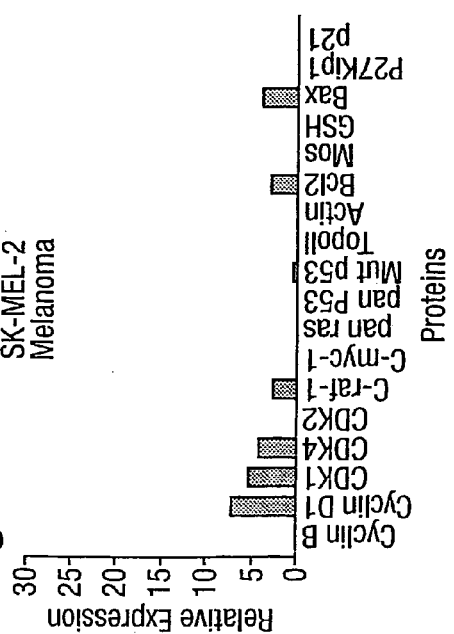
Figure 2:
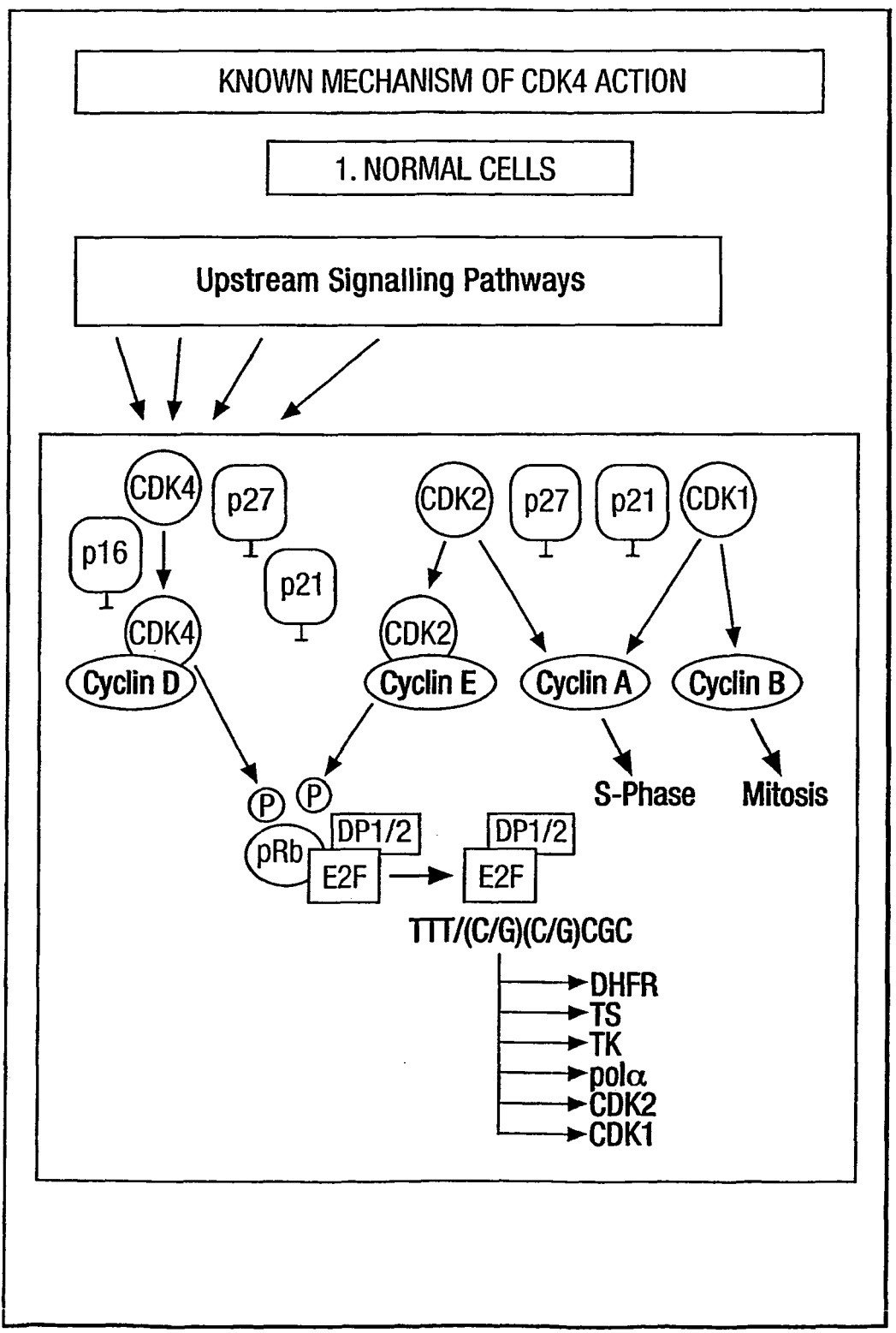
FIG. 2 is a schematic diagram showing the known mechanism of action of the CDK4 gene product in normal cells.

The present invention provides a method of screening for an agent, effective in the treatment of a cancer. The method generally comprises three steps.

The first step of the method is the selection of putative agents that are likely to disrupt a function mediated by a critical normal gene product, which function is required for the successful division and continued cell survival of cancer cells, and which function is not required for the successful division and continued cell survival of control cells. A critical normal gene product in the present context is a gene product which mediates a critical normal function i.e. a function required for the successful division and continued cell survival of cancer cells, which function is not required for the successful division and continued cell survival of non-cancerous control cells. Critical normal gene products are defined by two characteristics. Firstly, the product of a critical normal gene in the cancer sample must be either wild type (i.e. it has the same sequence as the gene product from a control sample, such as a sample of non-cancerous cells), or have no mutations that affect a critical normal function of the gene product. Where a critical normal gene product has a plurality of functions, it is only required that there are no mutations that affect a critical normal function of the gene product. A critical normal function of a critical normal gene product may be the same or different to a function of the gene product in normal cells. Secondly, the product of a critical normal gene in the cancer sample must be present in equal or higher amounts than in the control sample.

Critical normal gene products include factors which impede progress through the cell cycle, anti-apoptotic factors and master regulatory gene products which regulate the levels of gene products involved in the cell cycle and apoptosis pathways.

Factors which impede progress through the cell cycle include tumour suppressor gene products such as Rb protein, and CDK inhibitors such as the p27 protein. Anti-apoptotic factors include survivin protein, telomerase protein and gene products of the Bc1 family, such as Bc12. Master regulatory gene products which regulate the levels of gene products involved in the cell cycle and apoptosis pathways include the CDK1 and CDK4 gene products.

In the present invention, a cancer cell includes: a cell taken from a primary tumour, a metastasis or other suspected site of cancer in a subject, or a cell line derived from a cancer. A preferred embodiment is where the cancer cell is derived from a primary tumour, a metastasis, blood, urine, pleural effusions, ascites, faeces, cerebrospinal fluid or another sample from a patient believed to be suffering from cancer, especially malignancy. In addition, a cancer cell includes a cell taken from a cell line derived from a cancer. A preferred embodiment is where the cancer cell sample comprises induced cells derived from a cancer cell line transfected with a critical normal gene under the control of a regulatable promoter. A control cell includes a normal, non-cancerous cell and may be derived from the corresponding normal tissue of a patient, from any other normal tissue of a patient or from a primary cell line. In addition, control cells may be obtained from normal tissue or blood, urine, pleural effusion, ascites, cerebrospinal fluid and faecal samples from a subject not suffering from cancer. Uninduced cells derived from a cancer cell line transfected with a Critical Normal Gene under the control of a regulatable promoter may also be used as control cells.

The screen may be used to identify agents for cancers of any tissue or cell type. Advantageously, this includes common cancers such as breast, prostate, colon, bladder, stomach, pancreatic or oesophagus cancer, small cell lung cancer, non-small cell lung cancer, malignant melanomas, neuroblastomas and lymphomas.

In the present context, disruption of a function mediated by a critical normal gene product includes any disruption of a critical normal gene or the product of the gene which prevents a critical normal function of the product of the critical normal gene. This includes inhibiting production of the critical normal gene product or inhibiting the activity of the critical normal gene product that mediates the critical normal function.

Where the critical normal gene product has a plurality of functions, it is only required that disruption prevents critical normal functions of the gene product. Other functions of the gene product may also be affected.

Chemotherapeutic agents are preferred agents used in the screening method for effective agents that are cytotoxic to, and/or inhibiting to the growth of cancer cells. In the present invention, chemotherapeutic agents include antisense agents, ribozymes, peptides, proteins, antibodies, competitive and non-competitive inhibitors of the critical normal gene product and inhibitors of transcription or translation of the critical normal gene.

Antisense agents may be used to subtract the expression of a critical normal gene. It is possible to design antisense agents to bind to a particular gene using standard techniques. One technique is to use a computer program such as Amplify to select a set of antisense oligonucleotides that bind to the RNA target and that have the following characteristics (1) length between 10 and 35 bases (2) negligible self interaction under physiological conditions (3) melting temperature less than 40° C. under physiological conditions and (4) no more than 40% of the oligonucleotide being a run of guanines or cytosines. Using a reference such as Genbank, it can be ensured that the antisense oligonucleotides have less than or equal to 85% homology with the RNA transcripts of other genes. They can be synthesised using standard procedures.

Competitive and non-competitive inhibitors of the critical normal gene product are chemotherapeutic agents that can be used in the present invention. Where the critical normal function of the gene product is known, competitive inhibitors can be produced. Competitive inhibitors are molecules that resemble a target of the gene product. For example, where the critical normal gene product is a DNA binding protein, synthetic double-stranded oligonucleotides that contain the binding site for the DNA binding domain would be putative chemotherapeutic agents. Synthetic double stranded oligonucleotides can be produced by standard methods.

The screening method further comprises steps of testing the efficacy of the putative agents in samples of control and cancer cells and identification of effective agents.

Appropriate culture conditions for the cancer and control cells are used and the cultures are treated with the putative agent. Typically, those agents that are more cytotoxic to, and/or more inhibiting to the growth of, the cancer cell sample than the control cell sample are effective agents. Where the cancer cell sample comprises a cell from a cancer cell line transfected with a critical normal gene under the control of a regulatable promoter, agents can be tested against cells derived from the uninduced and induced cell line. Those agents that are more cytotoxic to, and/or more inhibiting to the growth of the induced cell sample than the uninduced cell sample are effective agents.

In one embodiment of the screening method, the cancer cell sample consists of one or more cancer cells in which the ratio of the levels of the CDK and CDK4 gene products is in the range of 0.6 to 1.6. In this embodiment, the step of identifying an effective agent further involves determination of the ratio the levels of the CDK1 and CDK4 gene products in the cancer cell sample before and after treatment with the putative agent. An effective agent is identified as an agent that is more cytotoxic or growth inhibiting to the cancer cell sample than the control cell sample and which is further capable of altering the ratio in the levels of the CDK1 and CDK4 gene product in a cancer cell sample.

The cancer cell sample consisting of one or more cancer cells in which the ratio of the levels of the CDK and CDK4 gene products is in the range of 0.6 to 1.6 is typically further characterised in consisting of one or more cancer cells in which the CDK1 and CDK4 gene products are both elevated as compared with control cells. In this case, the step of identifying an effective agent further involves determination of the levels of the CDK1 and CDK4 gene products in the cancer cell sample before and after treatment with the putative agent. An effective agent is defined as an agent that is more cytotoxic or more growth inhibiting to the cancer cell sample than the control cell sample and which is capable of reducing the levels of the CDKL and CDK4 gene products below those observed in the untreated cancer cell sample.

In the embodiments of the screening method in which the agent identified is capable of altering the ratio in the levels of the CDK1 and CDK4 gene product in a cancer cell sample, or in which the agent is capable of altering the ratio in the levels of the CDK1 and CDK4 gene product in a cancer cell sample, the critical normal gene product is preferably the CDK4 gene product, and more preferably the human CDK4 gene product. The function of the CDK4 gene product that is required for successful division and continued cell survival of cancer cells, which function is not required for the successful division and continued cell survival of control cells may be a function other than kinase activity.

The function of the human CDK4 gene product that mediates the critical normal function may be a region between amino acids 172-285.

Methods of measuring the levels of the CDK1 and CDK4 gene products from cell samples or extracts prepared from cell samples are well known to one skilled in the art. Suitable methods include Western blotting and FACS analysis using antibodies that bind to these gene products. Typically, two or more measurements are taken and a mean value is calculated for the cancer cell sample and the control cell sample, before and after treatment with the putative agent. The levels of the CDK1 and CDK4 gene products are considered to be elevated in cancer cells, if the mean levels of these gene products in the cancer cell sample (or extract) are higher than the mean levels of the gene products in the control cell sample (or extract). Similarly, the mean levels of the gene products in the cancer cell sample (or extract) before and after treatment can be compared to determine whether the agent is capable of reducing the levels of the CDK1 and CDK4 gene products below those observed in the untreated cancer cell sample.

The standard error of the mean may also be determined for the calculated mean values. These may be used to determine whether differences observed between the mean values of the levels of the CDK1 or CDK4 gene product in various samples or extracts are significant using statistical methods that are well known to one skilled in the art. For example, the levels of the CDK1 and CDK4 gene products may be considered to be elevated in cancer cells if the mean levels of these gene products in the cancer cell sample (or extract) are higher than the mean levels of the gene products in the control cell sample (or extract) plus one standard error. Preferably, two standard errors are added onto the mean value observed in the control cell sample, and more preferably, three standard errors are added. Similarly, the levels of the CDK1 and CDK4 gene products in the treated cancer cell sample may be considered to be reduced when compared to the untreated cancer cell sample (or extract), if the mean levels of these gene products in untreated cells minus one standard error is greater than the mean levels of the gene products in treated cells. Preferably, two standard deviations are subtracted, and more preferably three standard errors are subtracted.

The ratio of the mean levels of the CDK1 and CDK4 gene products may also be determined in the untreated cancer cell sample (or extract) and the treated cancer cell sample (or extract).

The screening method typically involves a step of further testing the effective agents identified in an animal model system. Where the animal is afflicted with the disease, the efficacy of the treatment and the side effects may be tested. Where normal animals are used, only the side effects may be tested.

In a further aspect, the present invention provides an agent for use in medicine, which agent is capable of disrupting a function of a critical normal gene product, which function is required for the successful division and continued cell survival of cancer cells, and which function is not required for the successful division and continued cell survival of control cells, and which agent is more cytotoxic to, or more inhibiting to the growth of a cancer cell sample than a control cell sample. Preferably, the critical normal gene product is a factor which impedes progress through the cell cycle, an anti-apoptotic factor or a master regulatory gene product which regulates the levels of gene products involved in the cell cycle and apoptosis pathways. Examples of critical normal gene products have been given above.

Agents of the invention may be identified by a screening method outlined above. An agent may also have further properties selected in these screens. For example, the agent may be capable of altering the ratio in the levels of the CDK1 and CDK4 gene products in the cancer cell sample from 0.6 to 1.6, to a ratio that does not fall within this range. Also, the agent may be capable of reducing the levels of the CDK1 and CDK4 gene product such that the levels in the treated cancer cell sample are below those observed in the untreated cancer cell sample.

The invention provides an agent according to the invention which disrupts a function of the human CDK4 gene product which function is required for the successful division and continued cell survival of cancer cells but not control cells, and is a function other than kinase activity. The region of the human CDK4 gene product that mediates the function required for successful division and continued cell survival may be a region between amino acids 172-285.

The agent of the invention may be an antisense oligonucleotide. For example, the agent may be an antisense agent having the sequence set out in SEQ ID NO:2. In another embodiment, the agent of the invention may be complementary to the region of the human CDK4 mRNA encoding amino acids 172-285, or a portion of the mRNA encoding three or more consecutive amino acids. Preferably, the antisense agent is complementary to four or more consecutive amino acids, more preferably, the antisense agent is complementary to five or more consecutive amino acids and more preferably, the antisense agent is complementary to 10 or more amino acids.

The agent of the invention may be used to treat cancers of various origins including breast, prostate, colon, bladder, stomach, pancreatic or oesophagus cancer, small cell lung cancer, non-small cell lung cancer, malignant melanomas, neuroblastomas and leukaemias.

Therefore, the present invention improves upon known methods of anticancer drug screening by providing effective drug targets. The conventional approach to anticancer drug development has identified a large number of potential drug targets, only some of which appear to be effective. In contrast, the present invention identifies a relatively few critical normal gene products which form effective drug targets. The drug targets are likely to be effective because the critical normal gene products, by definition, mediate functions that are required for continued cell division and survival. In addition, the screen of the present invention is not limited to targeting genes and gene products involved in early carcinogenesis. The screen targets gene products that play a role in the full malignant phenotype.

The present invention also solves the problems of tumour heterogeneity and genetic instability that complicated previous cancer therapies. Critical normal gene products whose function is essential for continued cancer cell survival and proliferation are likely to be homogeneous and stable throughout the tumour cell population. Loss of function of such critical normal gene products would remove the critical function they provided and result in cancer cell death. These gene products would thus be expected to be present and functional in every tumour cell and therefore provide a consistent anticancer drug target, unaffected by tumour heterogeneity and genetic instability. Drug resistance would thus not be a problem with new agents developed against critical normal gene product targets.

The invention also provides a pharmaceutical composition comprising an agent as described above and a carrier, diluent or excipient known in the art. A method of manufacturing a pharmaceutical composition is also provided, which method comprises a step of identifying an effective agent in the screening method of the invention and a step of manufacturing a pharmaceutical composition comprising said effective agent.

The agent of the invention and the pharmaceutical composition described herein may be used to treat cancer. All cancers may be treated by the agents and pharmaceutical compositions of the invention including breast, prostate, colon, bladder, stomach, pancreatic or oesophagus cancer, small cell lung cancer, non-small cell lung cancer, malignant melanoma, neuroblastoma or leukaemia.

In a further aspect, a method of treating a patient having cancer is provided. Such a treatment is tailored to the particular cancer and is more effective than known treatments. The method comprises the following steps:
  a) identifying a critical normal gene product present in said cancer; and
  b) treating the patient with an agent capable of disrupting a function mediated by said critical normal gene product, which function is required for the successful division and continued cell survival of cancer cells, and which function is not required for the successful division and continued cell survival of control cells, and which agent is an agent as described above.

The first method step is identification of the critical normal gene products present in the cancer. This step involves comparing putative critical normal gene products in a sample of cancer cells or an extract therefrom with a sample of control cells or an extract therefrom. As mentioned above, critical normal gene products are wild type in cancer cells (i.e. the gene product in the cancer sample has the same sequence as the gene product from the control sample, or has no mutations that affect the function critical to continued cancer cell survival and proliferation). Where a gene product has a plurality of functions, the gene product contains no mutations that affect the function critical normal function of the gene product. The critical normal function of a gene product may be totally distinct from the function of the gene product in normal cells. In addition, a critical normal gene product is present in equal or higher amounts in the cancer sample than in the control sample.

Gene products may be either RNA or protein. In the case of a gene that gives rise to a protein product, mRNA is produced as an intermediate. In such a case, either the mRNA or the protein can be tested to see whether the criteria for a critical normal gene product are met.

In the case where the gene product is an RNA, a three step test to identify a critical normal gene product is preferably employed. The first step is to measure the level of the gene product in both cancer and control samples. Determination of RNA levels can be effected in a number of ways, for example, by hybridising an oligonucleotide probe to the sample (Northern blotting; Slamon D J, Dekernion J B, Verma I M, Cline M J, Expression of cellular oncogenes in human malignancies, Science 224, 256-262) which methods would be routine to a person skilled in the art. One can readily convert poly-A bearing mRNA to cDNA using reverse transcription. It is also possible to reverse transcribe RNA without a poly-A tail by first ligating a poly-A tail to the 3' end of the RNA molecule. Reverse transcription PCR methods allow the quantity of single RNAs to be determined, but with a relatively low level of accuracy. Arrays of oligonucleotides are a relatively novel approach to nucleic acid analysis, and can be used to accurately measure the quantity of an RNA (Pease et al. (1994) Proc Natl Acad. Sci USA 91:5022-5026; Maskos and Southern (1993) Nucleic Acids Research 21: 2269-2270; Southern et al. (1994) Nucleic Acids Research 22: 1368-1373). The levels of the gene products in the two samples can then be compared. If the RNA is a critical normal gene product, the levels of RNA in the cancer sample must be greater than or equal to those in the control sample. As discussed in relation to comparing the levels of the CDK1 and CDK4 gene products, preferably two or more readings are taken and the mean levels of the putative critical normal gene product in the cancer cell sample (or extract) and control cell sample (or extract) are compared. Statistical methods can be used to determine whether the levels of the putative critical normal gene product are significantly different in the two samples.

The second step is to identify the sequence of the gene in both cancer and control samples. This can be done by sequencing cDNA produced from both samples by means of reverse transcription (see above). Also, arrays that measure both the expression levels of RNAs and detect mutations in those RNAs are being developed. Such arrays offer an attractive means to identify critical normal genes. The sequences should be compared. For the RNA to be the product of a critical normal gene, the RNA from the cancer sample must either be wild type (i.e. have the same sequence as the RNA from the control sample) or contain no mutations that affect the critical function of the gene product.

In the case where the putative critical normal gene product is a protein, the first step to identify a critical normal gene is to measure the protein levels in each sample. Methods of measuring protein levels would be well known to one skilled in the art. Measuring protein levels can be achieved by ELISA (Voller A, Bidwell D E, Bartlett A, 'The Enzyme Linked Immunoabsorbent Assay (ELISA). A guide with abstracts of microplate applications', Nuffield Laboratories of Comparative Medicine, the Zoological Society of London, Regent's Park London NW1. 1979. ISBN 0.906036.01.1. Sponsored by and available from Dynatech Europe, Borough House Rue du Pre, Guernsey, G B), Western Blotting (Stryer L, Exploring proteins Chapter 3 in Biochemistry $4^{th}$ Edition (1995) Ed. Lubert Stryer, W H Freeman and Company New York), FACS analysis/flow cytometry (Watson J, Stewart J, Cox H, Evan G, Sikora K, 'Flow cytometric quantisation of the c-myc oncoprotein Mol Cell Probes', 1, 1151-158) or immunocytochemistry techniques such as Western blotting (Stratton M R, Gusterson B, 'New techniques in pathology and their application in diagnosis and studies of tumour biology', Chapter 3.2 pp 350-362 in The Oxford Textbook of Oncology Volume 1 (1995) Eds. Michael Peckham, Herbert Pinedo and Umberto Veronesi, Oxford University Press, Oxford, New York, Tokyo). Proteomic chips and biosensor techniques may also be used in the present invention to measure protein levels. These techniques are both fast and sensitive.

The levels of the protein in the two samples can then be compared. If the protein is a critical normal gene product, the level of protein in the cancer sample must be greater than or equal to that in the control sample. As discussed in relation to comparing the levels of the CDK1 and CDK4 gene products, preferably two or more readings are taken and the mean levels of the putative critical normal gene product in the cancer cell sample (or extract) and control cell sample (or extract) are compared. Statistical methods can be used to determine whether the levels of the putative critical normal gene product are significantly different in the two samples.

The second step is to identify the sequence of the gene in both cancer and control samples. This can be done by either sequencing the gene as above, or by the use of antibodies specific to the wild type protein. For the protein to be the product of a critical normal gene, the gene from the cancer sample must either be wild type (i.e. have the same sequence as the gene from the control sample) or contain no mutations that affect the critical functioning of the protein in a cancer cell.

Examples of critical normal gene products identified using these methods are listed above.

For providing treatment tailored to a cancer patient, it is necessary to identify a critical normal gene that is present in the cancer. It is then possible to administer an agent capable of disrupting this critical normal gene or a pharmaceutical composition comprising this agent to the patient.

In a preferred embodiment, one or more additional critical normal gene products present in said cancer are identified and the method further comprises treating the patient with one or more additional agents capable of disrupting functions mediated by these critical normal gene products, which functions are required for successful division and continued cell survival of cancer cells, and which functions are not required for the successful division and continued cell survival of control cells.

The cancer treated by this method may be breast, prostate, colon, bladder, stomach, pancreatic or oesophagus cancer, small cell lung cancer, non-small cell lung cancer, malignant melanoma, neuroblastoma or a leukaemia. The cancer may be metastatic or non-metastatic.

The invention provides a method of selecting a suitable treatment for a patient having cancer, which method comprises identifying a critical normal gene present in said cancer as described above, followed by selecting an agent for treatment which agent is capable of disrupting a function mediated by said critical normal gene product, which function is required for the successful division and continued cell survival of cancer cell, and which function is not required for the successful division and continued cell survival of a control cell.

The method may further comprise identifying one or more additional critical normal gene products present in the cancer and selecting one or more additional agents capable of disrupting functions mediated by these critical normal gene products, which functions are required for successful division and continued cell survival of cancer cells and which functions are not required for the successful division and continued cell survival of control cells.

The agents or treatments selected for treatment in this method may be known agents or treatments.

Thus the present invention advantageously provides for selecting a treatment for a patient having cancer that is tailored to the genetic makeup of the cancer. This improves the efficacy of the treatment. In addition, it reduces the cost and delay resulting from selecting treatments that are not suitable for the cancer.

The present invention further provides a kit for selecting and providing a suitable treatment for a patient having a cancer. One such kit comprises:
 a) a means for identifying a critical normal gene product present in said cancer; and
 b) an agent capable of disrupting a function of said critical normal gene product which function is required for the successful division and continued cell survival of cancer cells but not control cells, and which agent is more cytotoxic to, or more inhibiting to the growth of a cancer cell sample than a control cell sample.

Examples of critical normal gene products are listed above.

Any means capable of identifying a critical normal gene product is suitable for inclusion in the kit. Preferably, the means for identifying a critical normal gene is an antibody that binds to said critical normal gene product.

Another embodiment of the invention provides a method of screening for an agent effective in preventing a cancer from undergoing metastasis, which method comprises:
 a) selecting a putative agent that is likely to disrupt a function mediated by a critical normal gene product for metastasis, which function is required for metastasis;
 b) determining the ability of a sample of metastatic cancer cells to undergo metastasis in the presence of said agent; and c) identifying an effective agent as an agent which, when present, reduces the ability of said sample of metastatic cancer cells to metastasise;

wherein said putative agent is a peptide or protein.

Preferably, the ability of the sample of metastatic cancer cells to metastasise is determined in the absence of said agent. The ability of metastatic cells to metastasise is reduced in the presence of an effective agent, but not in the absence of an effective agent.

Chemotherapeutic agents are preferred agents used in the screening method for effective agents that inhibit metastasis. In the present invention, chemotherapeutic agents include peptides and proteins. The peptides and proteins may be antibodies, competitive and non-competitive inhibitors of the critical normal gene product and inhibitors of transcription or translation of the critical normal gene.

Critical normal gene products for metastasis are defined by the same two characteristics that characterise critical normal gene products required for the successful proliferation and survival of cancer cells. Firstly, the product of a critical normal gene for metastasis in the cancer sample must either be wild type or have no mutations that affect the function of the gene product that is required for metastasis. Where the gene product has a plurality of functions, there must be no mutations that affect a function critical for metastasis. Secondly, the product of the critical normal gene must be present in equal or greater amounts than in the control sample.

Critical normal gene products for metastasis include proteases, proteins associated with cell adhesion (e.g. osteopontin), proteins associated with motility (e.g. p9Ka) and master regulatory gene products which regulate the levels of gene products involved in all aspects of carcinogenesis (e.g. CDK4).

RAMA37 cells transfected with the CDK4 gene undergo metastasis (Table 1). As the CDK4 gene products is elevated in the majority of cancer cells and as mutations in CDK4 are very rare (Example 4), CDK4 may act as a critical normal gene for metastasis.

Osteopontin is another normal protein that has been reported to be upregulated in cancer cells and to influence prognosis in prostate cancer (Hotte et al. (2002) Cancer 95: 506-512), breast cancer (Rudland et al. (2002) cancer Res. 62: 3417-3427), and a number of other tumours. Osteopontin acts as a critical normal gene product for metastasis in these cancer cells.

A sample of metastatic cancer cells may comprise one or more cancer cells derived from a metastasis present in subject suffering from cancer. A sample of metastatic cancer cells may comprise one or more cancer cells derived from a metastasis, a primary cancer or a cancer cell line that metastasises when introduced into an animal. The metastatic cancer cells may be cells derived from breast, prostate, colon, bladder, stomach, pancreatic or oesophagus cancer, small cell lung cancer, non-small cell lung cancer, malignant melanoma or a neuroblastoma.

The first step of the screening method is selecting an agent which is likely to disrupt a critical normal gene product. Chemotherapeutic agents and antisense agents are preferred agents in this embodiment. These may be designed to disrupt critical normal genes as described above.

The second step of the screening method involves determining the ability of a cancer cell sample to undergo metastasis in the presence of the agent. The method used to determine the ability of a cancer cell sample to undergo metastasis in the presence of an agent is not particularly limited and any suitable method may be used. In a preferred embodiment, the sample of cancer cells is injected into an animal model such as a rat. The agent is then administered to the animal model. The dosage of the agent may be determined by one skilled in the art. After a suitable period of time, the length of which may be determined by one skilled in the art, the animal is sacrificed and any metastases are identified. In a preferred embodiment, the animal model used is the nude mouse model described by Kojonniksen and colleagues (Kojonniksen et al. (1994) Cancer Res. 54: 1715-1719) or the nude rat model described by Weterman and co-workers (Weterman et al. Cancer Res. 52: 1291-1296).

The present invention also provides an agent for use in medicine, which agent is capable of disrupting a function of a critical normal gene product for metastasis in such a manner as to reduce the ability of a metastatic cancer cell sample to metastasise. Such an agent may be identified by the screening method for agents effective in inhibiting metastasis.

In a further aspect, the invention also provides a pharmaceutical composition comprising an agent as described above and medical uses of the agent and pharmaceutical composition.

Also provided is a method of treating a patient having metastatic cancer comprising:
a) identifying a critical normal gene product for metastasis present in said cancer; and
b) treating the patient with an agent capable of disrupting a function mediated by said critical normal gene product for metastasis, which function is required for metastasis.

As mentioned before, critical normal gene products for metastasis are wild type or have no mutations that affect the function of the gene product that is required for metastasis, and are present in the cancer cell sample in equal or greater amounts than in a control sample. Methods for identifying gene products that meet these criteria are outlined above. Once a critical normal gene product for metastasis has been identified, it patients may be treated with an agent that disrupts said critical normal gene product for metastasis. This agent may be a known agent or an agent identified in the screen for effective agents. The metastatic cancer may be a breast, prostate, colon, bladder, stomach, pancreatic or oesophagus cancer, small cell lung cancer, non-small cell lung cancer, malignant melanoma or a neuroblastoma.

In one embodiment, the method for treating a patient having metastatic cancer further comprises identifying one or more additional critical normal gene products for metastasis present in said cancer, and treating the patient with one or more additional agents capable of disrupting functions mediated by these critical normal gene products for metastasis, which functions are required for metastasis.

In a further aspect, the invention provides a method for selecting a treatment of a patient having metastatic cancer, which method comprises:
a) identifying a critical normal gene product for metastasis present in said cancer; and
b) selecting an agent for treatment, which agent is capable of disrupting a function mediated by said critical normal gene product for metastasis, which function is required for metastasis.

In one embodiment, the method for selecting a treatment for a patient having metastatic cancer further comprises identifying one or more additional critical normal gene products for metastasis present in said cancer, and selecting for treatment one or more additional agents capable of disrupting functions mediated by these critical normal gene products for metastasis, which functions are required for metastasis.

The invention also provides a kit for selecting and providing a suitable treatment for a patient having metastatic cancer comprising:
a) a means for identifying a critical normal gene product for metastasis present in said cancer; and
b) an agent capable of disrupting a function of said critical normal gene product which function is required for metastasis.

Any suitable means for identifying a critical normal gene product for metastasis may be used. In one embodiment, the means for identifying a critical normal gene product for metastasis may be an antibody that binds to the critical normal gene product for metastasis.

Another aspect of the invention concerns a method for analysing gene expression in dying cells. In particular, the invention provides an additional method for identifying a critical normal gene product which method involves comparing the levels of a gene product in dying and proliferating cancer cells. The method comprises:
a) detection of a gene product in L23COR cells that are quiescent or proliferating;
b) detection of said gene product in dying L23COR cells; and
c) identifying a critical normal gene as a gene product which is present at higher levels in quiescent or proliferating L23COR cells than in dying L23COR cells.

In the present invention, L23COR cells that are quiescent or proliferating encompasses L23COR cells within the cell cycle and L23COR cells in $G_0$ i.e. cells which are not dying. Quiescent or proliferating cancer cells are adherent to the surface of the tissue culture plate when grown in tissue culture. Dying L23COR cells do not adhere to the surface of the tissue culture plate when grown in tissue culture. One skilled in the art can separate adherent and non-adherent cells and can therefore separate quiescent or proliferating L23COR cells from dying L23COR cells. Gene expression in substantially pure populations of quiescent or proliferating L23COR cells, or dying L23COR cells can then be analysed by standard methods.

Typically, detection of a gene product will take place by FACS analysis, immunocytochemistry, Western Blotting or Northern Blotting, however, the method of detection is not particularly limited and any suitable method may be used.

The applicant arrived at the present invention by studying the genetic makeup of clinical cancers. The applicant realised that the severe damage in the cell division, differentiation, senescence and death pathways in the cells of a clinical tumour that progressively occur as the cancer evolves could potentially disrupt the normal function of these pathways so much that the cells become unable to undergo further cell division. Therefore, there may be certain gene products which are essential for continued cell survival and proliferation. This is consistent with the model of carcinogenesis proposed by Dr. Weinstein which indicates that that the disruption to the genes which normally regulate survival and cell proliferation during early carcinogenesis leads to the generation of a pattern of gene expression that is neither stable nor one that leads to cancer cell proliferation. The new gene expression pattern generated is thought to be essential for cancer cell proliferation and survival.

The applicant realised that the functions mediated by genes that are upregulated in cancer cells may be essential for the continued survival and proliferation of a cancer cell. The applicant also termed these genes "Critical Normal Genes". Critical normal genes remain wild type or contain no mutations that would affect a function of their product in cancer cells that is critical to the cancer cell, for example continued cancer cell survival and division. The products of such Critical normal genes assume a much more important role in the chaotic molecular environment of a typical clinical cancer cell than in a normal diploid cell. This is because in normal cells, the mechanisms controlling cell division, differentiation, senescence and death involve multiple, parallel positive and negative signalling pathways from the cell surface that interact with the molecular machinery controlling the cell cycle (Jones and Walker (1999) Mol Pathol. 52: 208-213; Hill (1999) Int. J. Biochem Cell Biol. 31:1249-1254; Miller et al. (1999) *Oncogene* 18:7860-7872; McCormick (1999) Trends Cell Biol. 9: 53-56; Lloyd et al. (1997) Genes and Development 11: 663-677). There is cross-talk between the components of these pathways which therefore function as a network (Mihich and Harlow (2000) Cancer Research 60: 7177-7183; Bhalla and Iyengar (1999) Science 283: 381-390; Kohn (1998) Oncogene 16: 1065-1075). So, in normal diploid cells, any individual critical normal gene would have a small role in the multiple interacting pathways controlling cell division and death. The progressive genetic damage that accrues during carcinogenesis results in cells in which the molecular mechanisms controlling cell growth and survival are not necessarily the same as those of normal diploid cells. This is known as bizarre cell circuitry (Weinstein (2000) Carcinogenesis 21:857-864). As fewer genes are involved, those gene products, whose continued functions are required for cancer cells to be able to divide, assume a greater importance as there is less redundancy.

The applicant realised that critical normal genes and critical normal gene products responsible for cancer cell survival and proliferation are potential anticancer drug targets because they are homogeneous and stable throughout the tumour cell population. If they were damaged, this would remove the critical function they provided, resulting in cancer cell death or a reduction in cancer cell proliferation. These gene products would thus be expected to be present and functional in every tumour cell and therefore provide a consistent anticancer drug target unaffected by tumour heterogeneity and genetic instability.

Given the considerable phenotypic variations in human clinical cancers, although critical normal gene products may exist, they may not always provide ubiquitous targets. The applicant realised that it would be necessary to identify what critical normal genes are present in a cancer in order to select a suitable treatment. In addition, the applicant realised that critical normal gene products common to all cancers may form a drug target that is present in all cancer cells. One critical normal gene product that may be present in all cancer cells is CDK4.

Similarly, the applicant realised that, due to the large number of mutations occurring, other processes carried out by cancer cells such as metastasis may also be affected by the large number of mutations present. The applicant identified gene products that must remain intact for metastasis to occur. Such critical normal genes for metastasis can be targeted to inhibit metastasis. As the majority of deaths from cancers of solid tissues are attributable to the process of metastasis, prevention of metastasis may greatly improve a cancer patient's prognosis.

Gene products often have numerous functions. Where this is the case, a critical normal gene product or a critical normal gene for metastasis may bear mutations in a region that is not responsible for mediating the critical normal function. The critical normal function of a gene product in a cancer cell may be distinct from the function of the gene product in normal cells.

As mentioned above, the CDK4 gene product may be a ubiquitous critical normal gene product. The CDK4-gene product has numerous functions; these include binding to cyclin D, binding to and phosphorylating pRb, binding to cyclin dependent kinase inhibitors such as p21, p27, p16 and other members of these families of CDKIs, interacting with a cyclin activating kinase and interacting with enzymes responsible, for phosphorylating and dephosphorylating tyrosine 17. In cancer cells, induction of CDK4 does not act to induce cells to progress from G1 to S phase and does not lead to phosphorylation of Rb. In fact, increasing levels of CDK4 protein increases the amount of hypophosphosrylated pRb. Therefore, CDK4 protein does not appear to perform its normal functions in cancer cells. This implies that some other function of CDK4 protein is critical to the survival of cancer cells.

Figure 3:
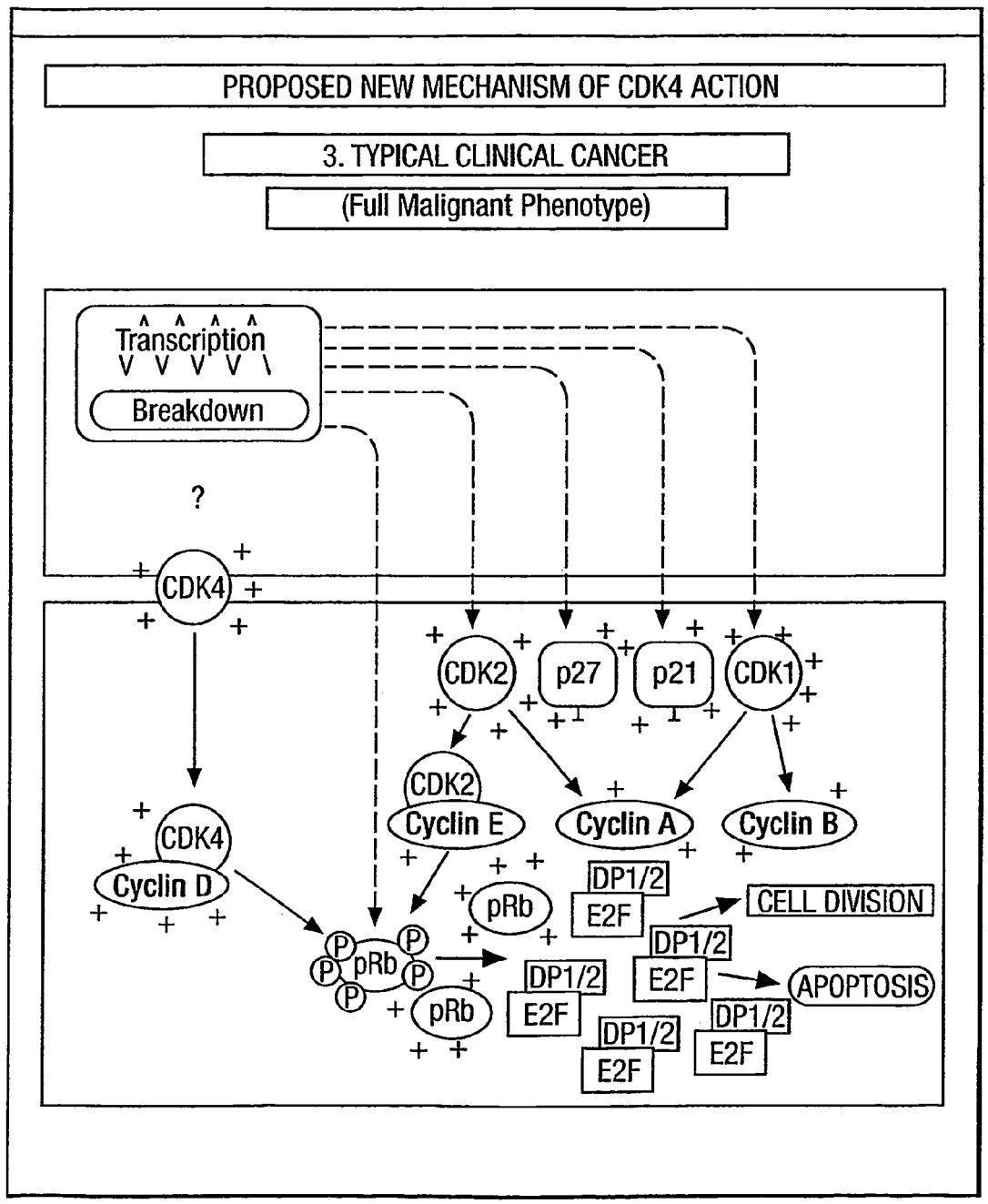
FIG. 3 is a schematic diagram showing a proposed new mechanism of action of the CDK4 gene product in a typical clinical cancer.
Figure 5:
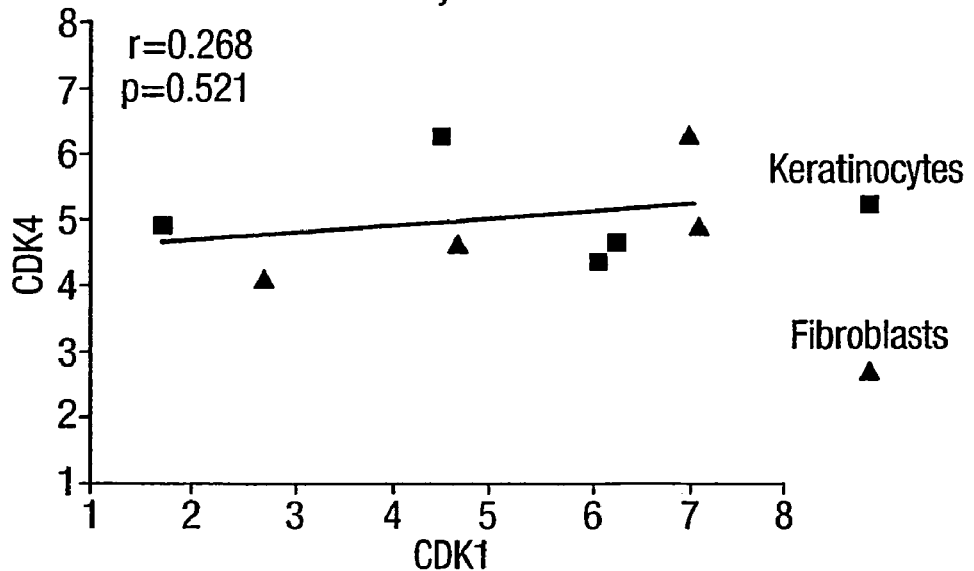
FIG. 5 shows the relationship between the CDK1 and CDK4 gene products in primary cultures of human fibroblast and keratinocyte cell lines. It can be seen that there is no correlation between the levels of these gene products in normal human cells.

The applicant has identified a novel function of the CDK4 gene product. The CDK4 gene product acts to elevate the level of CDK1 in cancer cells. The pathway by which the CDK4 gene product elevates the CDK1 gene product is not yet fully known but, without being bound by theory, appears to be independent of its: classical pathway of phosphorylating pRb. It is therefore a good candidate for mediating the critical normal function of the gene product. Without being bound by theory, the applicant considers that in the early stages of carcinogenesis, the CDK4 gene product has the same role as in normal cells. However, in cancer cells where there is severe disruption of normal function, the CDK4 gene product takes on a new role of promoting survival of otherwise very damaged cells by elevating levels of the CDK1 gene product. The CDK2, p27, p21, and Rb gene products are also co-elevated in human colorectal cancer. The applicant considers that the CDK4 gene product may also be responsible for upregulation of these gene products in cancer cells. The proposed mechanism of CDK4 in cancer cells is shown in FIG. 3. Many of the gene products upregulated by CDK4 are critical normal gene products. The applicant considers that this function of the CDK4 gene product may be critical to cancer cells in that it increases expression of other critical normal genes. These critical normal genes include those responsible for cancer cell survival and proliferation. CDK1, p27 and Rb are critical normal genes that are required for cancer cell survival and proliferation. The applicant considers that agents that disrupt this critical normal function of CDK4 may be effective anti-cancer agents.

Overexpression of CDK4 protein may also lead to metastasis. Elevation of CDK4 induces metastatic capability in RAMA37 cells (Table 2). In addition, overexpression of CDK4 protein leads to the elevation of the p9Ka protein. p9Ka protein has been shown to induce metastatic capability in non-metastatic mouse and rat mammary tumour cells (Davies et al. Oncogene (1993) 8: 999-1008; Grigorian et al. Int. J. Cancer (1996) 67: 831-841) and elevation of this protein may lead to metastasis.

Overexpression of CDK4 protein also leads to the elevation of critical normal gene products required for angiogenesis. Critical normal gene products required for angiogenesis include VEGF protein, FGF protein and TGF protein.

Analysis of the amino acid sequence of CDK4 indicates that a region near to the C-terminus (between 172 and 285) has no known function. The applicant postulates that this may be the region of the CDK4 gene product that mediates the novel critical normal function.

The experiments that lead the applicant to deduce that there is a novel critical normal function of CDK4 are described below. Details of the protocols used in the experiments are not intended to be limiting.

Experiment 1—Identification of a Relationship Between the Levels of the CDK1 and CDK4 Gene Products Twenty human cancer cell lines were cultured according to methods known in the art. Each cell culture was harvested using Trypsin/Versene (Sigma) and the cells were centrifuged at 250 G for 5 min. The supernatant from each centrifugate was decanted and the pellets were resuspended in PBS and the centrifugation repeated. Each cell pellet was then lysed at $3 \times 10^7$ cells per ml using a denaturing lysis buffer. The denaturing buffer was prepared by dissolving one tablet of complete Mini™ (Roche), a protease inhibitor cocktail, in 10 ml of a solution of 1% w/v SDS, 0.8% v/v Glycerol, 0.05M Tris (pH 6.8). The resultant lysates were sonicated on ice for 10 seconds, and the solutions were then centrifuged at 17,500 G for 30 minutes at 4° C. The supernatants were then aliquoted, and stored at −80° C.

The protein content of each lysate was determined using a Micro-BSA Protein Determination Kit (Pierce), and an amount of each lysate that contains an identical amount of protein was run on a discontinuous gel of 4% T, 2.6% C stacking gel, with a 10% T, 2.6% C resolving gel using the Lammelli system.

The resolved proteins were then transferred to a nitrocellulose membrane (Protran, Schleicher & Schuell) by electroblotting. Following electrophoretic transfer the membrane was 'blocked' for 1 hour with 10% w/v Marvel in TBS at room temperature. The membrane was then probed using a two-stage antibody detection method for a large number of proteins involved in the control of cell division and death. The proteins include CDK1, CDK2, CDK4, Cyclin D1, Cyclin B, $p27^{KIP1}$, p21WAF1, p53, Bcl2, Bax, Topoisomerase II, c-Myc, c-Raf-1, Pan RAS, MOS, GSH and actin (as a normal control). The amounts of each protein present in each lysate were quantified using the Phoretix software system (Phoretix 1D gel analysis from Non-Linear Dynamics Ltd.) and normalised against the mean level of the protein. The amounts of each protein in each cell line were then compared to one another by linear regression.

TABLE 1

|  | Actin | CDK1 | CDK4 | Cyclin D1 | pRb | Raf 1 | Ras | Myc | Topo IIa | Cyclin B | p27 |
|---|---|---|---|---|---|---|---|---|---|---|---|
| Actin |  | r = 0.01 | r = 0.08 | r = 0.13 | r = 0.21 | r = 0.41 | r = 0.28 | r = 0.13 | r = 0.36 | r = 0.12 | r = 0.09 |
|  |  | p = 0.96 | p = 0.75 | p = 0.59 | p = 0.52 | p = 0.08 | p = 0.23 | p = 0.59 | p = 0.12 | p = 0.67 | p = 0.77 |
| CDK1 | r = 0.13 |  | r = 0.84 | r = 0.12 | r = 0.22 | r = 0.28 | r = 0.24 | r = 0.40 | r = 0.18 | r = 0.34 | r = 0.55 |
|  | p = 0.58 |  | p = <0.0001 | p = 0.63 | p = 0.47 | p = 0.23 | p = 0.33 | p = 0.09 | p = 0.46 | p = 0.20 | p = 0.05 |
| CDK4 | r = 0.19 | r = 0.79 |  | r = 0.08 | r = 0.16 | r = 0.18 | r = 0.24 | r = 0.22 | r = 0.12 | r = 0.39 | r = 0.36 |
|  | p = 0.43 | p = <0.0001 |  | p = 0.75 | p = 0.61 | p = 0.46 | p = 0.33 | p = 0.38 | p = 0.63 | p = 0.14 | p = 0.23 |
| Cyclin D1 | r = 0.24 | r = 0.05 | r = 0.20 |  | r = 0.18 | r = 0.22 | r = 0.26 | r = 0.08 | r = 0.07 | r = 0.28 | r = 0.31 |
|  | p = 0.33 | p = 0.84 | p = 0.42 |  | p = 0.56 | p = 0.34 | p = 0.28 | p = 0.76 | p = 0.79 | p = 0.30 | p = 0.30 |
| pRb | r = 0.24 | r = 0.19 | r = 0.19 | r = 0.27 |  | r = 0.15 | r = 0.36 | r = 0.07 | r = 0.18 | r = 0.14 | r = 0.16 |
|  | p = 0.45 | p = 0.53 | p = 0.53 | p = 0.38 |  | p = 0.63 | p = 0.25 | p = 0.83 | p = 0.58 | p = 0.67 | p = 0.64 |

TABLE 1-continued

|  | Actin | CDK1 | CDK4 | Cyclin D1 | pRb | Raf 1 | Ras | Myc | Topo IIa | Cyclin B | p27 |
|---|---|---|---|---|---|---|---|---|---|---|---|
| Raf 1 | r = 0.37<br>p = 0.11 | r = 0.28<br>p = 0.23 | r = 0.17<br>p = 0.48 | r = 0.01<br>p = 0.97 | r = 0.06<br>p = 0.84 |  | r = 0.14<br>p = 0.55 | r = 0.26<br>p = 0.28 | r = 0.26<br>p = 0.27 | r = 0.28<br>p = 0.29 | r = 0.11<br>p = 0.73 |
| Ras | r = 0.19<br>p = 0.43 | r = 0.18<br>p = 0.46 | r = 0.20<br>p = 0.42 | r = 0.32<br>p = 0.19 | r = 0.41<br>p = 0.19 | r = 0.01<br>p = 0.96 |  | r = 0.23<br>p = 0.32 | r = 0.23<br>p = 0.34 | r = 0.10<br>p = 0.73 | r = 0.31<br>p = 0.32 |
| Myc | r = 0.02<br>p = 0.95 | r = 0.36<br>p = 0.13 | r = 0.27<br>p = 0.26 | r = 0.11<br>p = 0.66 | r = 0.11<br>p = 0.74 | r = 0.19<br>p = 0.43 | r = 0.27<br>p = 0.26 |  | r = 0.01<br>p = 0.95 | r = 0.01<br>p = 0.98 | r = 0.28<br>p = 0.39 |
| Topo IIa | r = 0.45<br>p = 0.05 | r = 0.07<br>p = 0.78 | r = 0.01<br>p = 0.95 | r = 0.03<br>p = 0.92 | r = 0.20<br>p = 0.54 | r = 0.27<br>p = 0.25 | r = 0.28<br>p = 0.23 | r = 0.10<br>p = 0.67 |  | r = 0.18<br>p = 0.51 | r = 0.05<br>p = 0.87 |
| Cyclin B | r = 0.26<br>p = 0.34 | r = 0.39<br>p = 0.13 | r = 0.46<br>p = 0.08 | r = 0.17<br>p = 0.54 | r = 0.07<br>p = 0.83 | r = 0.41<br>p = 0.11 | r = 0.01<br>p = 0.96 | r = 0.07<br>p = 0.81 | r = 0.46<br>p = 0.08 |  | r = 0.18<br>p = 0.60 |
| p27 | r = 0.15<br>p = 0.65 | r = 0.48<br>p = 0.09 | r = 0.23<br>p = 0.44 | r = 0.41<br>p = 0.16 | r = 0.05<br>p = 0.89 | r = 0.11<br>p = 0.73 | r = 0.23<br>p = 0.47 | r = 0.06<br>p = 0.86 | r = 0.22<br>p = 0.49 | r = 0.30<br>p = 0.37 |  |

FIG. 1 shows several histograms indicating the normalised expression levels of each of the genes tested in 20 human cell lines. It shows that each cancer cell has a unique pattern of gene expression.

Table 1 shows the results of the regression analysis. Table 1 shows that there is a strong positive correlation between the levels of the CDK1 gene product and the levels of the CDK 4gene product. The probability of such a correlation being observed by chance is less than 0.0001. No other significant correlations between the levels of different gene products have been observed.

Experiment 1—Generation of Human Expression Vectors Containing the CDK4 Open Reading Frame and a Human Ovarian Cancer Cell Line Containing the Expression Vector The human ovarian carcinoma cell line 2780 has amplified the CDK4 gene. It was therefore postulated that CDK4 mRNA would be abundant in this cell line. RNA was extracted from the cell line using the Tri Reagent (Sigma T9424) according to the manufacturer's instructions. The extracted RNA was then quantified spectrophotometrically. 1 µg of the RNA was reverse transcribed with SuperScript RT RNase H-Reverse Transcriptase. (Gibco BRL, 18053-17) using oligo (dT) as a primer. The resultant cDNA was used as a template for amplification of CDK4 DNA by reverse transcription PCR.

5 µl cDNA was amplified in 50 µl PCR reactions containing 20 pmoles of each primer using Taq DNA polymerase (Gibco BRL 18038-026). The reactions were placed in a pre-heated PCR block at 95° C. for 2 minutes before undergoing 30 cycles of denaturation (30 s at 95° C.), annealing (30 s at 65° C.) and extension (1 min at 72° C.). The length of the PCR products was checked on a 1% (w/v) agarose gel before being purified using Qiaquick PCR purification kit (Qiagen 28104). The purified DNA was used directly in sequencing reactions to ensure the whole wild-type CDK4 open reading frame was amplified.

Primers were designed to flank CDK4 cDNA. These primers were designed to incorporate the restriction enzyme sites EcoRI (Roche 1175 084) and NotI (Roche 1014 714) to allow the subsequent directional cloning of the amplified gene product into the multiple cloning site of the pcDNA3 vector (Invitrogen V790-20). The primers were synthesised by MWg Biotech.

(SEQ. ID NO.: 3)
5' CCC GAA TTC AGA ATG GTC ACC TCT CGA TAT GA 3'

(SEQ. ID NO.: 4)
5' CCC GCG GCC GCT GCT CAC TCT GGA TTA CCT T 3'

Sequencing primers (10 pmoles), identical to those employed in PCR reactions were radioactively labelled at their 5' ends with $\gamma^{32}$P-ATP (45 µCi). Sequencing was carried out using the f-mol DNA sequencing system (Promega—Q4100). It was found that the entire wild type CDK4 open reading frame had been amplified.

The CDK4 DNA and the plasmid vector pIND were digested sequentially with EcoRI and NotI according to the manufacturer's instructions. Bacteriophage T4 DNA ligase (New England Biolabs 202L) was used to ligate the digested CDK4 DNA to digested pIND. The ligated vector was used to transform E. coli. Transformants were selected by plating onto agar containing ampicillin. Colonies containing recombinant plasmids were identified by colony PCR and restriction analysis of minipreps of plasmid DNA, and then purified using the Concert Midi Prep Kit (GibcoBRL 11451-010).

The mammalian expression vector pVgRxR (Invitrogen) was transfected into, human ovarian cancer cell line 2780 using lipofection (lipofectamine plus Gibco cat no. 10964-013) or fuGENE 6 (Roche cat no 1-814 443) according to the manufacturer's instructions. Clones of cells surviving geneticin (G418 Gibco-BRI 10131-019) selection were then transfected with the pIND CDK4 construct, again using lipofection. Clones of cells surviving selection with zeocin (Invitrogen 45-0380) were then screened by PCR to check that they contained the CDK4 gene using the specific primers for the ecdysone/glucocorticoid response element. One clone generated in this manner was named 2780 1D/735. This clone is used in many of the following experiments.

Experiment 2—Determination of the Expression Levels of the CDK1 and CDK4 Gene Products Following Induction of 2780 1D/275

The level of CDK4 protein and CDK1 protein present in high, medium and low CDK4-expressing clones generated as described in Experiment 1 was determined at 24, 48 and 72 h following induction of CDK4 expression with ponasterone. At various time points after induction, the induced cells were harvested using Trypsin/Versene (Sigma). The harvested cells were centrifuged at 250 G for 5 min. The supernatant was decanted and the pellet was resuspended in PBS and the centrifugation was repeated. The cells were then lysed at $3 \times 10^7$ cells per ml using a denaturing lysis buffer. The denaturing buffer was prepared by dissolving one tablet of complete Mini™ (Roche), a protease inhibitor cocktail, in 10 ml of a solution of 1% w/v SDS, 0.8% v/v Glycerol, 0.05M Tris (pH 6.8). The resultant lysate was then sonicated on ice for 10 seconds, and this solution was then centrifuged at 17,500G for 30 minutes at 4° C. The supernatant was then aliquoted, and stored at −80° C.

The protein content of each lysate was determined using a Micro-BSA Protein Determination Kit (Pierce), and the lysates were run on a discontinuous gel of 4% T, 2.6% C stacking gel, with a 10% T, 2.6% C resolving gel using the Lammelli system.

The resolved proteins were then transferred to a nitrocellulose membrane (Protran, Schleicher & Schuell) by electroblotting. Following electrophoretic transfer the membrane was 'blocked' for 1 hour with 10% w/v Marvel in TBS at room temperature. The membrane was then probed using a two-stage antibody detection method. The first stage used antibodies generated to human CDK1$^{cdc2}$ (cdc2 p37 (17), Santa Cruz, cat. no. Sc-54) and human CDK4 (CDK4 (c-22), Santa Cruz, cat. no. Sc-260). The second stage involved the subsequent probing of the membrane using Horse Radish Peroxidase conjugated Sheep anti-mouse IgG (Serotec, cat. no. AAC10P) for CDK1, and Horse Radish Peroxidase conjugated Sheep anti-rabbit IgG (Serotec, cat. no. STAR54) for CDK4. The protein bands were then detected using Luninol based Chemoluminescent reagent ECL™ Western blotting detection reagent Kit (from Amersham pharmacia biotech, cat. no. RPN2106), and Hyperfilm™ MP (from Amersham pharmacia biotech, cat. no. RPN1675K). The protein band signals obtained following probing of the membranes as described above were then analysed using the Phoretix software system (Phoretix 1D Gel Analysis, from Non Linear Dynamics Ltd).

The results are presented in FIG. 6. The figure clearly shows that the level of the CDK1 gene product increases as the level of CDK4 rises within the cells of each clone. The figure also shows that the levels of the CDK1 and CDK4 gene products are present in an approximately 1:1 ratio. FIG. 6 shows that the levels of these proteins are not related in normal fibroblast and keratinocyte cells. Without being bound by theory, the applicant hypothesises that the mechanism by which the CDK4 gene product elevates the level of the CDK1 gene product includes a feedback mechanism that ensures that the levels of the two proteins are approximately equal.

Experiment 3—Elisa Assay Showing the CDK1 and CDK4 Gene Products are Co-Elevated in 2780 1D/275 Following Induction Cells of clone 2780 1D/275 were plated at a density of 20000 cells/well into a 96 well flat bottomed TC plate (Costar) in 100 µl of medium (Hams F12 medium+5 mM Glutamine) containing 10% FBS. The plate was incubated overnight at 37° C. in 5% $CO_2$. 100 µl medium plus 10% FBS plus 5 µM pontasterone was then added to the test wells. 100 ml medium plus 10% FBS was added to control wells. The plate was then incubated as above for 48 hours. The medium was then removed and each well was washed three times with 100 µl PBS. The samples were then fixed for 30 minutes by addition of 2% paraformaldehyde in PBS. The wells were then washed three times in ELISA wash buffer (40 g NaCl, 1 g KCl, 14.5 g $Na_2HPO_4.12H_2O$, 1 g $KH_2PO4$ in 5 L distilled water). Each wash lasted 5 minutes. The wells were blocked with 1% BSA in ELISA wash buffer for 20 min. The wells were then washed once with wash buffer (Standard ELISA wash Buffer containing 0.1% Tween 20).

To measure the level of CDK4 protein produced by the ponasterone induced cells, a first antibody solution consisting of 100 µl of a 1 in 1000 dilution of anti-CDK4 (Santa Cruz Rabbit polyclonal to CDK4) in PBS was added to the test wells. No first antibody was added to the control wells. The plate was then incubated for 1 hour at 37° C. The cells were then washed three times with wash buffer. Each wash lasted 5 min. To measure the degree of binding of the first antibody, 100 µl of a second antibody solution consisting of a 1 in 1000 dilution of a Goat anti-Rabbit Horse Radish Peroxidase Conjugated antibody was added to each well (both test and control wells) and the plate was incubated for 1 h at 37° C. The wells were then washed three times with wash buffer as described above. The cells were developed with DAB (Dako DAB Tablets) DAB for 30 min. The reaction was stopped with 4% $H_2SO_4$. Each well was read at 450 nm on Biorad plate reader. The experiments were repeated using anti-CDK1 as the primary antibody.

Figure 7:
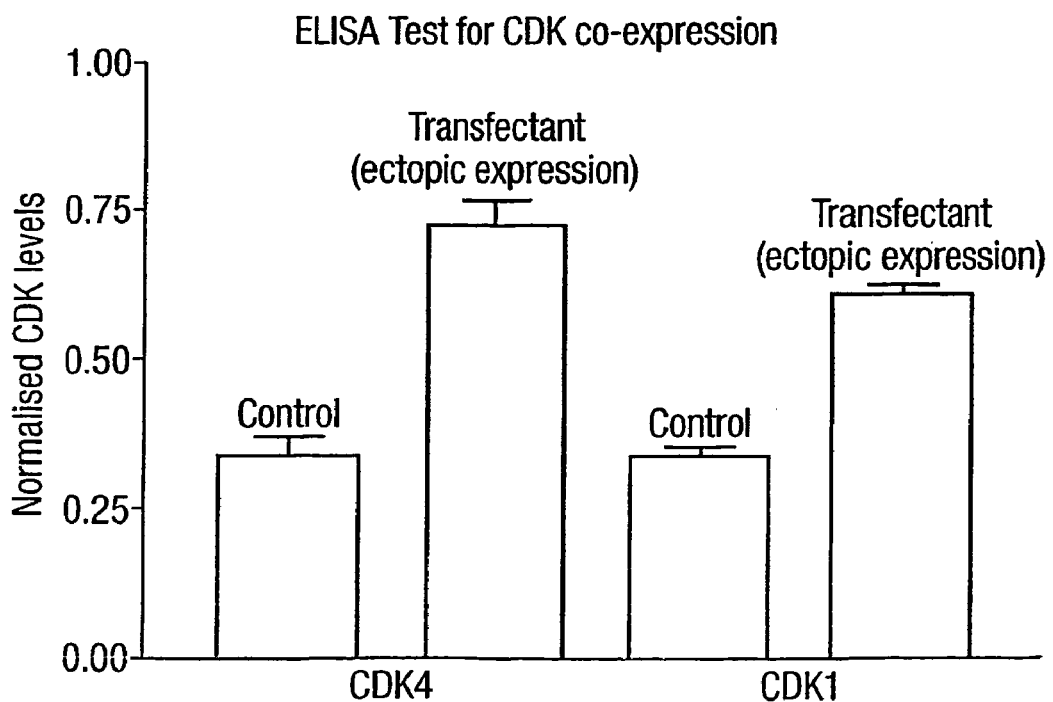
FIG. 7 shows the results of an ELISA assay that measured the levels of the CDK1 and CDK4 gene products in ponasterone-induced and uninduced clone 2870 1D/735. It can be seen that the levels of both the CDK4 gene product and the CDK1 gene product are elevated 48 h after induction/mock induction.

FIG. 7 shows that the CDK1 and CDK4 gene products are co-elevated in 2780 1D/275 48 h after ponasterone induction of transfected exogenous CDK4 DNA.

Experiment 4—CDK1/CDK4 Ratio in Proliferating and Dying Human Cancer Cells

L23COR (a human non-small cell lung cancer cell line) was grown as a monolayer attached to the bottom of a tissue culture flask. The cells shed from the confluent monolayer were collected, transferred to a flask and their fate was followed for several days. The detached cells underwent spontaneous cell death. Detached L23COR cells provide a model for dying human cancer cells. This model was used to analyse the molecular changes that occur when human cancer cells die.

L23COR cells were cultured. The culture medium (containing the detached cells) was removed and centrifuged at 250G for 5 min. The adherent cells were washed with medium and then harvested using Trypsin/Versene (Sigma). The harvested cells were centrifuged at 250 G for 5 min. Both the adherent cell pellet and the detached cell pellet was resuspended in PBS and the centrifugation was repeated. The cells were then lysed at $0.3 \times 10^7$ cells per ml using a denaturing lysis buffer. The denaturing buffer was prepared by dissolving one tablet of complete Mini™ (Roche), a protease inhibitor cocktail, in 10 ml of a solution of 1% w/v SDS, 0.8% v/v Glycerol, 0.05M Tris (pH 6.8). The resultant lysate was then sonicated on ice for 10 seconds, and this solution was then centrifuged at 17,500 G for 30 minutes at 4° C. The supernatant was then aliquoted, and stored at −80° C.

The protein content of each lysate was determined using a Micro-BSA Protein Determination Kit (Pierce), and the lysates were run on a discontinuous gel of 4% T, 2.6% C stacking gel, with a 110% T, 2.6% C resolving gel using the Lammelli system.

The resolved proteins were then transferred to a nitrocellulose membrane (Protran, Schleicher & Schuell) by electroblotting. Following electrophoretic transfer the membrane was 'blocked' for 1 hour with 10%/w/v Marvel in TBS at room temperature.

The membrane was then probed using a two-stage antibody detection method. The first stage used antibodies generated to human CDK1$^{cdc2}$ (cdc2 p37 (17), Santa Cruz, cat. no. Sc-54) and human CDK4 (CDK4 (c-22), Santa Cruz, cat. no. Sc-260). The second stage involved the subsequent probing of the membrane using Horse Radish Peroxidase conjugated Sheep anti-mouse IgG (Serotec, cat. no. AAC10P) for CDK1, and Horse Radish Peroxidase conjugated Sheep anti-rabbit IgG (Serotec, cat. no. STAR54) for CDK4. The protein bands were then detected using Luminol based Chemoluminescent reagent ECL™. Western blotting detection reagent Kit (from Amersham pharmacia biotech, cat. no. RPN2106), and Hyperfilm MP (from Amersham pharmacia biotech, cat. no. RPN1675K). The protein band signals obtained following probing of the membranes as described above were then analysed using the Phoretix software system (Phoretix 1D Gel Analysis, from Non Linear Dynamics Ltd).

FIG. 8 shows that the level of the CDK1 gene product in the detached (dying) cells is lower than that in the adherent (proliferating) cells. In contrast, the level of the CDK4 gene product in the detached cells is approximately twice as high as the level of the CDK4 gene product in adherent cells. Without being bound by theory, the applicant hypothesises that in cancer cells, the CDK4 gene product upregulates the CDK1 gene product. The CDK1 gene product (directly or indirectly) forms part of a negative feedback loop that regulates the levels of the CDK4 gene product. Therefore, in normal cancer cells, the ratio between the levels of the CDK1 and CDK4 gene products is in the range of 0.6 to 1.6. FIG. 8 shows that proliferating L23COR cells exhibit a CDK1/CDK4 ratio of approximately 1.0. When cancer cells die, the process by which CDK4 elevation results in CDK1 elevation is disrupted. As CDK1 levels reduce, the levels of CDK4 increase unchecked distorting the ratio of the CDK1 and CDK4 gene products. FIG. 8 shows that the detached cells exhibit a CDK1/CDK4 ratio of about 0.3. The detached cells may die because the level of the CDK1 gene product is insufficient to phosphorylate survivin at mitosis leading to apoptosis (see Example 4).

This data supports the model that co-elevated CDK1/CDK4 performs a critical normal function in cancer cells, which, when lost leads to death of the cancer cells.

Experiment 5—Cell Cycle Distribution of Induced and Uninduced 2780 1D/275

The cell cycle distribution of uninduced and ponasterone-induced 2780 1D 275 was analysed using flow cytometry.

Asynchronously growing monolayers of uninduced and induced 2780 1D/275 at 24 h and 72 h after induction/mock induction were harvested using Trypsin/Versene solution (Sigma). The cell suspension was then centrifuged in Falcon tubes (Becton Dickinson) at 250 G, for 5 minutes. The supernatant was then removed by pipette. The cell pellet was then resuspended in PBS, and the sample re-centrifuged. The supernatant was then removed by pipette, and the pellet resuspended by passing through a 200 µl Finnpipette tip repeatedly. The cells were then fixed in 70% v/v Ethanol in water, and stored at 4° C. overnight.

The fixed samples were centrifuged at 250 G for 5 minutes, and the supernatant was removed by pipetting. The cell pellet was then resuspended in PBS, and then centrifuged for 5 minutes at 250 G. The supernatant was then removed by pipetting, and the cells stained in a solution containing 20 ug·ml$^{-1}$ RNase A, and 10 ug·ml$^{-1}$ Propidium iodide. The samples were then incubated for 30 minutes at 37° C.

Stained samples were then analysed using a Becton Dickinson FACScan, using a 488 nm Argon laser, with the Lysis II data acquisition software running of Consort 32.

FIG. 9 shows that the uninduced and induced cultures have similar DNA content profiles at 24 and 72 hours following induction. It can be seen that at 24 h after induction, both the uninduced and induced culture have equal numbers of (~8 times as many) cells in G1 as G2. After 72 hours, this ratio has increased to 34 in both induced and uninduced 2780 1D cells. Thus, CDK4 expression does not appear to alter the cell cycle distribution.

Experiment 6—Bivariate Analysis of CDK4 and CDK1 Expression Throughout the Cell Cycle Asynchronously cultured monolayers of uninduced and ponasterone induced 2780 1D/275 were harvested using Trypsin/Versene (Sigma), and the cell suspension was the centrifuged at 250 G for 5 minutes in a Falcon Tube (Becton Dickinson). The supernatant was then removed by pipetting, and the cell pellet resuspended in PBS. The sample was then centrifuged for a further 5 minutes at 250 G. The supernatant was again removed by pipetting and the cell pellet was resuspended by repeated passage through a 200 µl Finnpipette tip. The cells were then fixed in Methanol overnight at −20° C.

The Methanol fixed samples were centrifuged, the supernatant was discarded, and the pellet resuspended in PBS. The cell suspensions were then centrifuged at 250 G for 5 minutes, and the supernatant removed by pipetting.

The cell pellet was then resuspended by gentle agitation, and the cells were then stained using 2 µg of rabbit anti human CDK4 FITC conjugated antibody (Cdk4 (C-22) FITC, cat no. sc-260 FITC, Santa Cruz Biotechnology) per 1×10$^6$ cells, or 2 µg of mouse anti human CDK1 FITC conjugated antibody (Cdc2 p34 (17) FITC, cat no. sc-54 FITC, Santa Cruz Biotechnology) per 1×10$^6$ cells. The cells were then incubated at room temperature for 1 hour in the dark.

The samples were then counter-stained with 5 µg of Propidium Iodide, and incubated for 30 minutes with 20 µg of RNase A. Stained samples were then analysed using a Becton Dickinson FACScan, using a 488 nm Argon laser, with the Lysis II data acquisition software running off a Consort 32. Data was collected on the FL3 channel (red fluorescence) to determine the DNA content of the cell population, and FL1 channel to determine the level and distribution of the CDK1 and CDK4 proteins.

The List Mode Data obtained from the FACScan was translated into DOS using HP-LIF to DOS conversion package, DataMate (Verity, Applied Cytometry Systems). The CDK1 and CDK4 cell cycle distributions were determined by bivariate analysis using the Multiple Document Interface WIN MDI (Shareware).

The results are shown in FIG. 10. Panel A shows the level of CDK4 protein in the uninduced culture at different stages of the cell cycle. It can be seen that most cells are in G1 phase. Panel A also shows that CDK4 protein is expressed in all phases of the cell cycle viz G1, S, G2/M. Panel B shows the same data for the induced culture. It can be seen that the CDK4 protein content of all cells is higher irrespective of which phase of the cell cycle they occupy. There is, however no change in the relative distributions of cells in each cell cycle phase. Panels C and D show similar data for CDK1 protein. CDK1 protein is elevated in response to induction of CDK4 in G1, S and G2/M cell cycle phases. The relative distribution of the cells in each cell cycle phase is similar in the uninduced and induced cultures.

Experiment 7—Determination of the Phosphorylation Status of RB Family Members in Uninduced and Induced Cultures of 2780 1D/275

Rb p105 is the hypophosphorylated form of pRb which binds E2F/DP transcription factors. Rb p110 is the hyperphosphorylated form of pRb. pRb is hyperphosphorylated by CDK4 protein in normal cells and releases free E2F/DP to initiate transcription of a wide range of genes required for cell division.

The level of Rb p110 and Rb p105 present in uninduced and ponasterone induced 2780 1D/275 at various times after transfection was determined using SDS PAGE and Western blotting. At various time points after transfection, the transfected cells were harvested using Trypsin/Versene (Sigma). The harvested cells were centrifuged at 250 G for 5 min. The supernatant was decanted and the pellet was resuspended in PBS and the centrifugation was repeated. The cells were then lysed at 3×10$^7$ cells per ml using a denaturing lysis buffer. The denaturing buffer was prepared by dissolving one tablet of complete Mini™ (Roche), a protease inhibitor cocktail, in 10 ml of a solution of 1% w/v SDS, 0.8% v/v Glycerol, 0.05M Tris (pH 6.8). The resultant lysate was then sonicated on ice for 10 seconds, and this solution was then centrifuged at 17,500 G for 30 minutes at 4° C. The supernatant was then aliquoted, and stored at −80° C.

The protein content of each lysate was determined using a Micro-BSA Protein Determination Kit (Pierce), and the lysates were run on a discontinuous gel of 4% T, 2.6% C stacking gel, with a 10% T, 2.6% C resolving gel using the Lammelli system.

The resolved proteins were then transferred to a nitrocellulose membrane (Protran, Schleicher & Schuell) by electroblotting. Following electrophoretic transfer the membranes were 'blocked' for 1 hour with 10% w/v Marvel in TBS at room temperature. The membranes were then probed using a two-stage antibody detection method. The first stage used antibodies generated to human p110 (Mouse monoclonal antibody IF8, Santa Cruz Biotechnology) and p105 (Mouse monoclonal antibody NCL-RB_358, Novacastra). The second stage involved the subsequent probing of the membrane using Horse Radish Peroxidase conjugated Sheep anti-mouse IgG (Serotec, cat. no. AAC10P). The protein bands were then detected using Luminol based Chemoluminescent reagent ECL™ Western blotting detection reagent Kit (from Amersham pharmacia biotech, cat. no. RPN2106), and Hyperfilm™ MP (from Amersham pharmacia biotech, cat. no. RPN1675K). The protein band signals obtained following probing of the membranes as described above were then analysed using the Phoretix software system (Phoretix 1D Gel Analysis, from Non Linear Dynamics Ltd).

Panel A of FIG. 11 shows that a low level of hyperphosphorylated p110 is present at all time points in transfected cells which have not been ponasterone stimulated. Panel A also shows that there is no increase in the levels of hyperphosphorylated pRb (p110) phosphorylation with time following ponasterone induction of CDK4 expression. Instead, hyperphosphorylated pRb (p110) is virtually undetectable in induced cells. Panel B of FIG. 10 shows that in uninduced cells, most CDK4 is present in the phosphorylated (p110) form. However, 24 h and 48 h after ponasterone induction, hypophosphorylated p105 becomes apparent in transfected cells.

Experiment 8—Determination of Metastasis Ability RAMA37 cells Transfected with Human CDK4 DNA.

RAMA37 cells (derived from immortalised normal rat mammary epithelial cells) were transfected with a mammalian expression construct comprising the human CDK4 ORF in pcDNA3. As controls, pcDNA3 vector alone and pcDNA3 containing the human p53 ORF were transfected into RAMA37 cells.

Transfectants were selected with neomycin and then cultured. The transfected cell lines were tested for mRNA and protein expression by Northern and Western Blotting respectively to detect transfectants expressing increased levels of the transfected genes. The high expressing cells lines were grown up in tissue culture to yield sufficient cells for inoculation into animals.

$2 \times 10^6$ cells of each transfected cell line were inoculated into a single site subcutaneously into each of 20 female Furth Wistar rats. The rats were sacrificed and metastasis was detected by removal and macroscopic inspection of the rat lungs. The results are shown in Table 2.

TABLE 2

| Transfectant cell line | Tumours at inoculation site | Metastasis |
|---|---|---|
| PcDNA3 | 14/20 | 0/14 |
| p53pcDNA3 | 7/20 | 0/7 |
| CDK4pcDNA3 | 10/20 | 9/10 |

Table 2 clearly shows that RAMA37 cells expressing increased levels of CDK4 give a high incidence of pulmonary metastases.

Experiment 9—Western Blot Showing Changes in p9Ka Expression Following Induction of CDK4 Expression.

The level of CDK4 protein and p9Ka protein present in uninduced and induced 2780 1D/275 generated was determined at 24, 40 and 48 h following induction of CDK4 expression with ponasterone or mock induction. At 20, 40 and 48 h after induction/mock induction, the induced cells were harvested using Trypsin/Versene (Sigma). The harvested cells were centrifuged at 250 G for 5 min. The supernatant was decanted and the pellet was resuspended in PBS and the centrifugation was repeated. The cells were then lysed at $3 \times 10^7$ cells per ml using a denaturing lysis buffer. The denaturing buffer was prepared by dissolving one tablet of complete Mini™ (Roche), a protease inhibitor cocktail, in 10 ml of a solution of 1% w/v SDS, 0.8% V/v Glycerol, 0.05M Tris (pH 6.8). The resultant lysate was then sonicated on ice for 10 seconds, and this solution was then centrifuged at 17,500 G for 30 minutes at 4° C. The supernatant was then aliquoted, and stored at −80° C.

The protein content of each lysate was determined using a Micro-BSA Protein Determination Kit (Pierce), and the lysates were run on a discontinuous gel of 4% T, 2.6% C stacking gel, with a 10% T, 2.6% C resolving gel using the Lammelli system. Prestained markers were run on either side of the samples The resolved proteins were then transferred to a nitrocellulose membrane (Protran, Schleicher & Schuell) by electroblotting. Following electrophoretic transfer the membrane was cut across the 27 kilodalton molecular weight marker. The membranes were 'blocked' for 1 hour with 10% w/v Marvel in TBS at room temperature. The upper portion of the membrane was probed using a two-stage antibody detection method. The first stage involved probing the membrane with a 1 in 250 dilution of an antibody raised against human CDK4 (Santa Cruz, cat. no. Sc-260) for 1 h at room temperature. The second stage involved the subsequent probing of the membrane using a 1 in 1000 dilution of Horse Radish Peroxidase conjugated Sheep anti-rabbit IgG (Serotec, cat. no. STAR54). The protein bands were then detected using Luminol based Chemoluminescent reagent ECL™ Western blotting detection reagent Kit (from Amersham pharmacia biotech, cat. no. RPN2106), and Hyperfilm™ MP (from Amersham pharmacia biotech, cat. no. RPN1675K).

The lower portion of the membrane was probed with a 1 in 1000 dilution of rabbit anti-human p9ka polyclonal antibody (DAKO A5114) for 16 hours at room temperature. The second stage involved the subsequent probing of the membrane using a 1 in 1000 dilution of Horse Radish Peroxidase conjugated Sheep anti-rabbit IgG (Serotec, cat. no. STAR54). The protein bands were then detected using Luminol based Chemoluminescent reagent ECL™ Western blotting detection reagent Kit (from Amersham pharmacia biotech, cat. no. RPN2106), and Hyperfilm™ MP (from Amersham pharmacia biotech, cat. no. RPN1675K).

Figure 12:
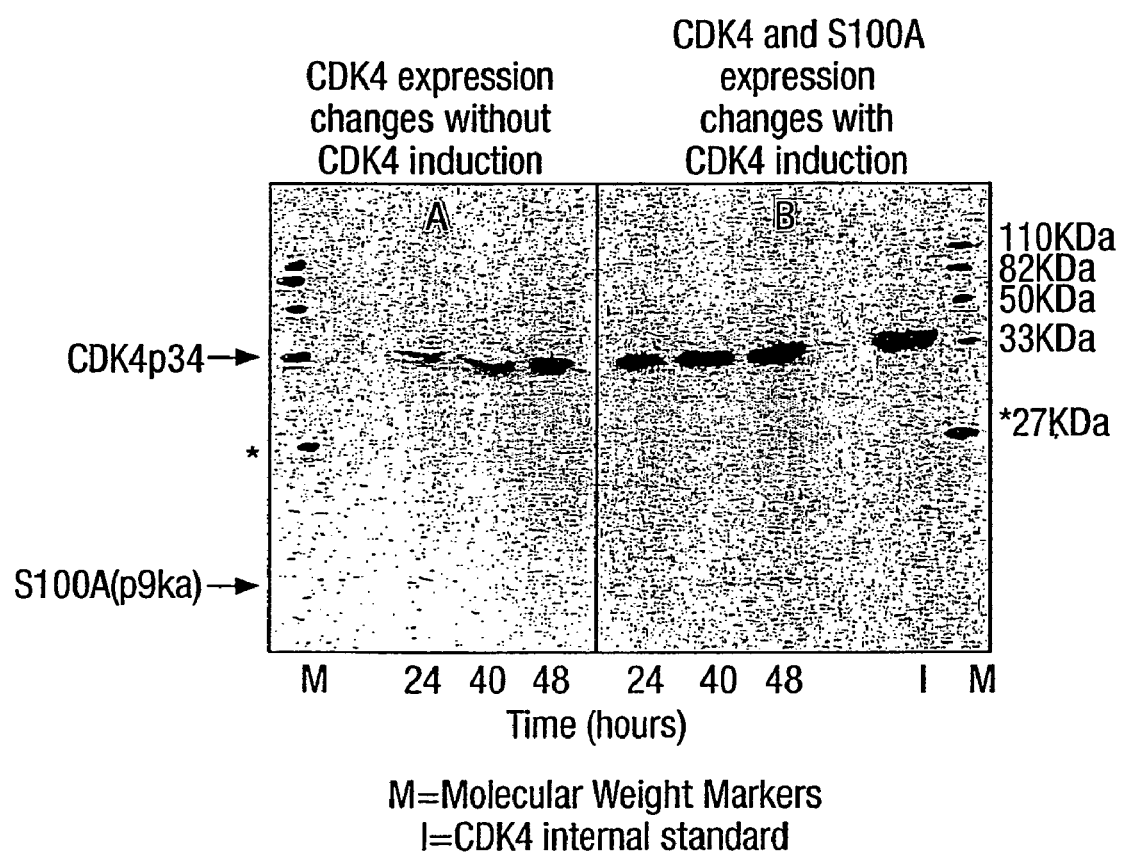
FIG. 12 shows western blots of samples of ponasterone induced and uninduced clone 2780 1D/735 at 24, 40 and 48 h after induction/mock induction. Panel A shows the blots of the uninduced samples and Panel B shows the results for the induced samples. The upper portion of each panel is probed with an antibody specific for CDK4 protein. The lower portion of each panel is probed with an antibody specific for p9Ka protein. Panel A shows that CDK4 protein (p110) is present at a low level in the uninduced samples. p9Ka protein is undetectable in the uninduced samples. In the induced samples, CDK4 protein is present at a higher level than in the uninduced samples. The level of CDK4 protein also increases with time post induction. p9Ka is detectable in the induced samples and increases with time post induction.

The results are presented in FIG. 12. Panel A shows that p9ka protein is undetectable at 20, 40 and 48 following mock induction. CDK4 protein is present in all uninduced samples in an approximately equal amount. The amount of CDK4 protein in each sample of panel B is greater than the level in the uninduced cell lysates. In addition, the level of CDK4 protein increases with induction time. Small amounts of p9Ka protein are present. These also increase with longer induction times. Without being bound by theory, the applicant hypothesises that the CDK4 gene product elevates the level of the p9Ka gene product.

The invention will be described further with the aid of Examples. These examples illustrate the scope of the invention but are not intended to be limiting.

EXAMPLES

Example 1

Identification of p27$^{KIP1}$ Protein as a Critical Normal Gene Product p27$^{KIP1}$ mutations have not been found, or are extremely rare in various cancers (Sgambato et al. (2000) J. Cell Physiol. 183: 18-27). In addition, the protein product of this gene is paradoxically upregulated in human mammary cancer cell lines and primary human cancers of the breast (Weinstein (2000) Carcinogenesis 21: 857-864). Upregulation has also been reported in a subset of human cancers including oesophagus, breast, colon and small cell lung cancers (Fredersdorf et al. (1997) Proc Natl. Acad. Sci 94: 6380-6385; Yatabe et al. (1998) Cancer Res. 58: 1042-1047). Whereas p27$^{KIP1}$ protein levels fluctuate throughout the cell cycle in normal mammary epithelium, they remain high throughout the cell cycle in breast cancer cell lines (Sgambato et al. (1997) Clin Cancer Res. 3: 1879-1887). This implies that p27$^{KIP1}$ protein functions as a critical normal gene product in some breast, colon, oesophagus and small cell lung cancers. Therefore, chemotherapeutic agents that target the p27$^{KIP1}$ gene product are likely to prove suitable chemotherapeutic agents for the treatment of these cancers.

This is unexpected as p27$^{KIP1}$ protein functions as an inhibitor of cell division in normal cells. Before the realisation that p27$^{KIP1}$ protein was a critical normal gene product, it would not have been obvious to treat cancer by disrupting an inhibitor of cell division. The applicant considers that p27$^{KIP1}$ may act as a critical normal gene by promoting apoptosis. Increasing expression of p27$^{KIP1}$ protein by retroviral transduction (Banerji et al. (2001) Oncogene 20: 7352-7367; Li et al. (2000) World J. Gastroenterol. 6: 513-521) or transfection of zinc inducible p27 causes G1 cell cycle arrest and subsequent apoptosis. p27$^{KIP1}$ induced apoptosis has been shown to be associated with inhibition of CDK2 complexed to cyclin E (Masuda et al. (2001) Am. J. Pathol. 158: 87-96) or cyclin A (Hiromura et al. (1999) J. Clin. Invest. 103: 597-604). p27$^{KIP1}$ protein may, however, function as a critical normal gene product by an alternative mechanism to that of causing apoptosis as high levels of p27$^{KIP1}$ protein has been reported to be related to poor prognosis but not an increased apoptotic index in colorectal adenocarcinomas (Tenjo et al., (2000) Oncology 58: 45-51).

As discussed above, the applicant hypothesises that in clinical cancers there is a state of chaos where the normal complex mechanistic controls of cell division and death no longer operate. Instead, the cellular fate is determined by the non-stochastic balance of expression of genes promoting cellular proliferation with those promoting cell death. This cell death may be by apoptosis as has been reported to occur as a result of E2F overexpression but could also take the form of necrosis. Cell proliferation and apoptosis may both be consequences of E2F overexpression. For tumours to survive and proliferate there would be expected to be controlling gene products maintaining E2F at levels which promoted cell division but not apoptosis. Exerting such control is suggested to be a potential function of critical normal gene products. Without being bound by theory, the applicant postulates that p27$^{KIP1}$ protein is involved in controlling the level of E2F.

p27$^{KIP1}$ protein does not act as a critical normal gene product in all cancers. Many aggressive, poorly differentiated tumours (including certain lymphomas, gliomas, small cell lung cancers and cancers of the breast, stomach, colon, prostate and oral cavity) display reduced expression of p27$^{KIP1}$ protein. Tumours for which anti-p27$^{KIP1}$ treatment would be suitable may be identified by a two step test. The first step involves measuring the level of p27$^{KIP1}$ mRNA or p27$^{KIP1}$ protein in a sample of cancer cells or an extract therefrom, and in a control sample as described above. The level of mRNA or protein in the cancer sample must be greater than or equal to that in the control sample for anti-p27$^{KIP1}$ treatment to be suitable. The second step is to identify the sequence of p27$^{KIP1}$ in both tumour and control samples. This can be done by either sequencing the gene, or by the use of antibodies specific to the wild type protein. For anti-p27$^{KIP1}$ treatment to be suitable, the gene from the cancer sample must be wild type (i.e. have the same sequence as the gene from the control sample) or contain no mutations that affect the critical functioning of the protein. Antisense cDNA to p27$^{KIP1}$ mRNA or direct inhibitors of the p27$^{KIP1}$ protein are likely to be effective chemotherapeutic agents for treatment of tumours in which p27$^{KIP1}$ is a critical normal gene product.

Example 2

Identification of Chemotherapeutic Agents for Cancers in which Retinoblastoma is a Critical Normal Gene Retinoblastoma has been reported to be elevated in human leukaemias and breast colon and bladder cancers (Weinstein (2000) Carcinogenesis 21: 857-864; Wildrick and Boman (1994) Mol Carcinogenesis 10: 1-7). Furthermore, a progressive increase in the expression of pRb protein has been found during the multistage process of colon carcinogenesis (Yamamoto et al. (1999) Clin Cancer Research 5: 1805-1815). Thus, pRb is a critical normal gene product in such cells.

The applicant postulates that pRb acts as a critical normal gene product in cancer cells in which it is upregulated by inhibiting apoptosis. Apoptosis occurs as a consequence of overexpressed E2F-1 in the full malignant phenotype. Through its interaction with E2F, pRb may inhibit the apoptotic pathway (Harbour and Dean, (2000) Nature Cell Biol. 2: E65-67). Lack of pRb protein has been shown to correlate with increased sensitivity to UV radiation induced apoptosis in human breast cancer cells (Carlson and Ethier (2000) Radiat. Res. 154: 590-599) whilst transduction with pRb containing adenovirus Ad-Rb attenuates p53 induced apoptosis in cervical cancer cell lines (Ip et al., (2001) Eur. J. Cancer 37: 2475-2483). These studies support the hypothesis that pRb acts as a critical normal gene product by protecting cancer cells from apoptosis.

```
SEQ 1:      5'-GTCATGCCGCCCAAAACC-3'

SEQ 2:      5'-GGTTTTGGGCGGCATGAC-3'
```

Sense and antisense phosphorothionate oligonucleotide with the sequence set out in SEQ1 and SEQ2 respectively were synthesised in a 380B DNA synthesiser. Each oligonucleotide was premixed with lipofectin reagent and diluted in DMEM (Gibco). 6 cm plates of HCT116 cells at 40-50% confluence were rinsed once with 4 ml serum free DMEM and transfected with the oligonucleotides at a final concentration of 1 μM and the lipofectin reagent at a final concentration of 19 μg/ml according to the manufacturer's instructions (Life Technologies Inc., Gaithersburg, Md.). After 4 hours, Foetal Calf Serum (Gibco) was added to a final concentration of 10%. A lipofectin only transfection was performed as a control. Cell extracts were harvested after 48 h and examined by Western blot analysis with a pRb antibody. Equal loading of protein samples was confirmed by Coomassie blue staining or by immunoreactivity with an anti-actin antibody (Sigma). The intensities of the Rb bands were quantised with an image scanner (Molecular Dynamics). The results show that treatment of the cells with the antisense oligonucleotide reduced the level of pRb expression to about 30% of the control culture treated only with lipofectin. The treatment with the sense oligonucleotide led to about a 5% reduction in the level of pRb. Growth curves indicated that the culture treated with the antisense oligonucleotide displayed growth inhibition when compared with the lipofectin-treated control culture; but that treatment with the sense oligonucleotide had no significant effect on growth. Apoptosis in the cultures 48 h after transfection was tested for using the TUNEL assay. An in situ apoptosis detection kit ApopTag (Oncor, Gaithersburg, Md.) was used as recommended by the manufacturer. The percentage of TUNEL positive cells was 1.5+/−1% for the lipofectin treated culture, 3+/−0.5% for the culture transfected with the sense oligonucleotide and 18+/−0.5% for the culture transfected with the antisense oligonucleotide. Thus, the sense oligonucleotide caused about a two-fold increase in apoptosis, but the antisense oligonucleotide caused over a 10-fold increase in apoptosis. As the antisense oligonucleotide inhibits growth and increases apoptosis, it is thus an effective chemotherapeutic agent.

The retinoblastoma gene is not a ubiquitous critical normal gene as it is inactivated in a large number of human cancers. Tumours for which anti-Rb treatment would be suitable may be identified by a two step test. The first step involves measuring the level of Rb in a sample of cancer cells or an extract therefrom, and in a control sample. This can be achieved by measuring levels of Rb protein or mRNA as described above. The level of protein in the cancer sample must be greater than or equal to that in the control sample for anti-Rb treatment to be suitable. The second step is to identify the sequence of Rb in both tumour and control samples. This can be done by either sequencing the gene, or by the use of antibodies specific to the wild type protein. For anti-Rb treatment to be suitable, the gene from the cancer sample must be wild type (i.e. have the same sequence as the gene from the control sample) or contain no mutations that affect the critical functioning of the protein. For such tumours, the antisense agent with the sequence set out in SEQ2 is likely to be an effective chemotherapeutic agent.

Example 3

Identification of p9Ka Protein as a Critical Normal Gene Product for Metastasis

3 µm tissue sections were cut from archival formalin-fixed paraffin embedded specimens from 287 patients who had presented with primary operable breast cancer between the years 1976 to 1982 in the Merseyside Region as reported previously (Winstanley et al. Br. J. Cancer (1991) 63: 447-450). The tissue sections were dewaxed (Warburton et al. J. Histochem. Cytochem. (19.82) 30: 667-676) endogenous peroxidase activity was blocked with $H_2O_2$ (Streefkerk J. Histochem. Cytochem. (1972) 20: 829-831), and the p9Ka antigen was visualised by the ABC method (Hsu et al. J. Histochem Cytochem (1981) 29: 577-580) using horseradish peroxidase and diethylaminobenzene to produce a brown colouration on the histological sections. The cell nuclei were counterstained blue by Meyers Haemalum (Warburton et al J. Histochem. Cytochem. (1982) 30: 667-676). The percentage of carcinoma cells stained for p9Ka protein was determined from two sections of each specimen, 5 to 10 fields per section (250× magnification; about 200-400 cells) in a microscope by two independent observers. In sections from 107 patients, <1% of the carcinoma cells were stained for p9Ka protein, in sections from 45 patients, 1-5% of the carcinoma cells were stained for p9Ka protein, and in 135 patients, >5% of the carcinoma cells were stained for p9Ka protein.

Therefore, in a large number of primary breast cancers, p9Ka protein is expressed or overexpressed by the cancer cells. Overexpression of p9Ka has been suggested to be associated with metastatic spread to local lymph nodes in human breast cancer (Albertazzi et al. DNA Cell Biol. (1998) 17: 335-342), and shown to be present in liver metastases arising from colon carcinomas (Takenaga et al. Clin Cancer Res. (1997) 3: 2309-2316). This implies that p9Ka protein must be present in cells at normal levels or higher for metastasis to occur. In support of this hypothesis, p9Ka protein has been shown to induce metastatic capability in non-metastatic rat and mouse mammary tumour cells (Davies et al. Oncogene (1993) 67: 999-1008; Grigorian et al. Int. J. Cancer (1996) 67: 831-841) and to co-operate with oncogenic changes in non-metastatic tumour cells to yield metastatic tumours (Ambartsumian et al. Oncogene (1996) 13: 1621-1630; Davies et al. Oncogene (1996) 13: 1631-1637).

Anti-p9Ka treatment may prevent tumours expressing p9Ka metastasising. As the process of metastasis is responsible for the majority of deaths arising from cancers of solid tissues, treatment with anti-p9Ka may reduce mortality. Tumours for which anti-p9Ka treatment would be suitable may be identified by a two step test. The first step involves measuring the level of p9Ka mRNA or p9Ka protein in a sample of cancer cells or an extract therefrom, and in a control sample as described above. The level of mRNA or protein in the cancer sample must be greater than or equal to that in the control sample for anti-p9Ka treatment to be suitable. The second step is to identify the sequence of p9Ka in both tumour and control samples. This can be done by either sequencing the gene, or by the use of antibodies specific to the wild type protein. For anti-p9KA treatment to be suitable, the gene from the cancer sample must be wild type (i.e. have the same sequence as the gene from the control sample) or contain no mutations that affect the critical function of the protein. Antisense cDNA to p9KA mRNA or direct inhibitors of the p9Ka protein are likely to be effective chemotherapeutic agents for treatment of tumours in which p9Ka is a critical normal gene product.

Example 4

Identification of CDK1 and CDK4 as Ubiquitous Critical Normal Genes

The CDK1 and CDK4 proteins have been shown to be consistently co-elevated in a wide range of human cancer cell lines (Seabra and Warenius (1998) Proc Am Ass Cancer Research 39: 442). In Seabra and Warenius, the levels of the CDK1 and CDK4 gene products in every cell line were greater than those in normal fibroblast or keratinocytes. The ratio in the levels of the CDK1 and CDK4 gene products in these cells lines was also 0.6-1.6. Similar co-elevation of these proteins has also been observed in clinical samples of human colon and breast cancers as compared to adjacent normal tissue. The CDK4/CDK1 relationship found in human cancer cells (Warenius (2002) Anticancer Res. In press) is not present in normal keratinocytes and fibroblasts (FIG. 4).

No mutations have been recorded in CDK1 in the literature to date and the only mutation that has been recorded in CDK4 is rare and involves the p16$^{INK4}$ binding regions of the protein (Sotillo et al, (2001) EMBO J. 20: 6637-47); Rane et al (2002) Mol. Cell. Biol. 22: 644-56) which would make CDK4 refactory to p16$^{INK4}$ inhibition but not necessarily disrupt any other CDK4 functions. In fact, transgenic mice engineered to carry this mutation (replacement of Arg 24 by Cys) have embryonic fibroblasts which show escape from cellular senescence and increased tumorigenesis. Thus, this mutation does not appear to prevent a critical normal function of the CDK4 gene product.

Thus, the CDK1 and CDK4 genes meet the criteria defining a critical normal gene. They are overexpressed in cancer cells and remain wild type or do not have any mutations that affect the critical normal function of the protein. Cancer cells which do not overexpress these gene products in a ratio of 0.6 to 1.6 undergo cell death. In support of this assertion, FIG. 8 shows that dying L23COR cells exhibit a CDK1/CDK4 ratio of 0.3 whilst proliferating L23COR cells have a CDK1/CDK4 ratio of 1.0. Therefore, it appears that if the critical normal function of CDK1 and CDK4 is removed from cancer cells, the cancer cells undergo cell death. This is evidence that these gene products perform a critical normal function within human cancer cells. As a large number of cancers show co-elevation of CDK1 and CDK4 proteins (see table 1), the CDK1 and CDK4 gene products may be more ubiquitous targets for novel anticancer drug development. Antisense oligonucleotides complementary to CDK1 or CDK4 mRNA may thus be effective chemotherapeutic agents.

The critical normal function of the CDK1 gene product may be to prevent apoptosis and thereby promote tumour cell survival. Increased expression of CDK1 and a significantly decreased apoptotic index have both been detected in recurrent as compared to primary colonic tumours (Seong et al., (1999) Int. J. Radiat. Biol. Phys 45: 1167-73). Moreover, inhibition of CDK1 protein with olomucine and roscovitine results in increased levels of apoptosis (Schutte et al., (1997) Exp. Cell Res. 236: 4-15). Without being bound by theory, the applicant considers that CDK1 protein may regulate apoptosis through phosphorylation of survivin at mitotis. Phosphorylation of survivin prevents dissociation of survivin-caspase 9 complex on the mitotic apparatus and thus prevents the release of caspase 9 which promotes apoptosis (O'Conner et al., (2000) Proc. Natl. Acad. Sci., USA 97: 13103-13107). The region of the CDK1 gene product that interacts with survivin is likely to be a good target for chemotherapeutic agents.

The applicant has identified a critical normal function of the CDK4 gene product in cancer cells. It appears that CDK4 acts to elevate CDK1, p9Ka and possibly CDK2, CDK6 and p27 by a mechanism that is independent of its role in the cell cycle. The region of CDK4 protein that mediates this function is unknown. CDK4 protein has many known functional regions with regard to its action in normal cells (see FIG. 3). These involve regions responsible for binding to Cyclin D, p16$^{INK4}$, p27$^{KIP1}$, p21$^{WAF1/CIP1}$ and pRb. There are also regions carrying out CDK kinase functions. These include the CDK4 site which phosphorylates pRb, Tyrosine 17 whose phosphorylation/dephosphorylation by kinases and phosphatases controls CDK4 kinase activity, and Threonine 164 whose phosphorylation is required for the activation of CDK4 kinase. The novel function of CDK4 in clinical cancer cells described here does not involve the known functions of the regions described above. The applicant suggests, without being bound by theory, that the relatively long length of peptide between amino acids 172 and 285 of the CDK4 protein, to which no function has yet been ascribed, contains further functional regions which may be involved in the mechanism by which CDK4 causes elevation of CDK1, p9Ka, hypophosphorylated pRb, CDK2, p27KIP1 and possibly other critical normal gene products in human clinical cancer cells. Inhibitors to this region of the protein are likely to be effective agents for the treatment of cancer. Antisense agents complementary to the region of the CDK4 mRNA encoding amino acids 172-285 are likely to be effective agents for the treatment of cancer.

The experimental data presented in this application suggests that the critical normal function of the CDK4 gene product resides in its ability to elevate the levels of other critical normal genes which are crucial for the survival of cancer cells and metastasis.

The CDK4 gene product is known to bind to p9Ka. The applicant hypothesises that CDK4 and 9Ka may, in combination, promote metastasis. In support of this, RAMA 37 cells (derived from a rat mammary cell line) transfected with either p9Ka DNA or with CDK4 DNA are able to metastasise in an assay for metastasis whilst untransfected cells do not metastasise (see Table 1).

Example 5

Identification of Telomerase as a Ubiquitous Critical Normal Gene

Telomerase is silent in most adult normal tissues (except stem cells), but is re-expressed in all tumours where it is required to overcome the telomere shortening which accompanies each cell division (Preston (1997) Rad. Research 147: 529-534). It therefore acts as a Critical Normal Gene Product. Telomere shortening ultimately leads to cancer cell death. Telomerase inhibitors remove the capacity of cancer cells to regenerate telomeres and thus to undergo unlimited proliferation. The efficacy of telomerase inhibitors would be expected however to be dependent upon telomere length at the time treatment is implemented. Advanced tumours with long telomeres and within only a few doublings of the tumour load required to kill the patient would be less likely to be arrested by anti-telomerase treatment before they caused death than early tumours which would have undergo may more doublings and telomere shortenings to produce the same outcome. Thus whilst telomerase potentially provides a ubiquitous critical normal gene product target in terms of gene expression, therapeutic strategies directed at this target may not be effective in all tumours.

The invention claimed is:

1. A method of screening for an agent effective in the treatment of a cancer, which method comprises:
   a) selecting a putative agent that is likely to disrupt a function mediated by a critical normal gene product, which function is required for the successful division and continued cell survival of cancer cells, and which function is not required for the successful division and continued cell survival of control cells;
   b) determining the ratio of CDK1 and CDK4 gene products in the cancer cells before treatment with the putative agent;
   c) treating a cancer cell sample and a control cell sample with the putative agent wherein the cancer cell sample consists of one or more cancer cells in which the ratio of the levels of the CDK1 and CDK4 gene products is in the range of 0.6 to 1.6, and determining the cytotoxic effect of, and/or the growth inhibiting effect of the putative agent on these samples;
   c) determining the ratio of CDK1 and CDK4 gene products in the cancer cells after treatment with the putative agent; and
   d) identifying an effective agent as an agent which is more cytotoxic to, and/or more inhibiting to the growth of the cancer cell sample than the control cell sample, wherein an effective agent is identified as an agent capable of increasing the ratio in the levels of the CDK1 and CDK4 gene product in a cancer cell sample treated with the putative agent compared to untreated cancer cells.

2. The method according to claim 1, wherein the critical normal gene product is a factor which impedes progress through the cell cycle, an anti-apoptotic factor or a master regulatory gene product which regulates the levels of other gene products involved in the cell cycle and apoptosis pathways.

3. A method according to claim 1, wherein the cancer cell sample consists of cells in which the CDK1 and CDK4 gene products are both elevated as compared with control cells.

4. A method according to claim 1, wherein the critical normal gene product is human CDK4.

* * * * *